(12) United States Patent
Louie et al.

(10) Patent No.: US 8,224,664 B1
(45) Date of Patent: *Jul. 17, 2012

(54) PORTABLE PRESCRIPTION ORDER DISTRIBUTION CART AND TRACKING SYSTEM

(75) Inventors: Shelton Louie, Vancouver, WA (US); Stephen A. Garrett, Vancouver, WA (US)

(73) Assignee: GSL Solutions, Inc., Vancouver, WA (US)

( * ) Notice: Subject to any disclaimer, the term of this patent is extended or adjusted under 35 U.S.C. 154(b) by 1557 days.

This patent is subject to a terminal disclaimer.

(21) Appl. No.: 10/928,758

(22) Filed: Aug. 26, 2004

Related U.S. Application Data

(63) Continuation-in-part of application No. 10/925,360, filed on Aug. 23, 2004, now abandoned, and a continuation-in-part of application No. 10/223,308, filed on Aug. 18, 2002, now Pat. No. 7,887,146, and a continuation-in-part of application No. 10/223,336, filed on Aug. 18, 2002, now abandoned, and a continuation-in-part of application No. 09/991,530, filed on Nov. 16, 2001, now abandoned, and a continuation-in-part of application No. 09/991,249, filed on Nov. 16, 2001, now abandoned, and a continuation-in-part of application No. 09/991,529, filed on Nov. 16, 2001, now Pat. No. 7,496,521, and a continuation-in-part of application No. 09/829,536, filed on Apr. 9, 2001, now abandoned, and a continuation-in-part of application No. 09/715,439, filed on Nov. 16, 2000, now Pat. No. 7,672,859.

(60) Provisional application No. 60/496,829, filed on Aug. 21, 2003.

(51) Int. Cl.
*G06Q 10/00* (2012.01)

(52) U.S. Cl. .................................. 705/2; 705/3
(58) Field of Classification Search ................... 705/2–3
See application file for complete search history.

(56) References Cited

U.S. PATENT DOCUMENTS 404,458 A     6/1889   Woodruff
(Continued)

FOREIGN PATENT DOCUMENTS

EP        0 899 677        3/1999
(Continued)

OTHER PUBLICATIONS

White, Ron, How Computers Work, Millenium Ed., Que Corporation, Sep. 22, 1999.

(Continued)

*Primary Examiner* — Vivek Koppikar
*Assistant Examiner* — Rajiv Raj
(74) *Attorney, Agent, or Firm* — Harness, Dickey & Pierce, PLC

(57) ABSTRACT

A portable cart and related system for operating the cart to automatically detect and track a prescription orders through distribution, particularly within a health-care facility is disclosed. A unique wireless tag is operably secured to each prescription order, and tag readers, which are in communication with a computer system, are positioned near the cart and, if needed, throughout the facility, to detect the presence of a tag within a defined physical area. Preferably, unique tags are also operably secured to each worker and patient. The system this detected information to track the prescription order and preferably verify the proper distribution of the prescription order to the correct patient. More preferably, the system also records, or charts, the distribution event.

24 Claims, 18 Drawing Sheets

U.S. PATENT DOCUMENTS

| | | |
|---|---|---|
| 827,649 A | 7/1906 | Murphy |
| 1,236,324 A | 8/1917 | Leonard |
| 1,592,497 A | 7/1926 | Mays |
| 1,750,291 A | 3/1930 | Whetstone |
| 1,993,477 A | 3/1935 | Glenn et al. |
| 2,174,068 A | 9/1939 | Citron |
| 2,962,335 A | 11/1960 | Benson |
| 3,167,873 A | 2/1965 | Toms |
| 3,172,711 A | 3/1965 | Gillotte |
| 3,744,867 A | 7/1973 | Shaw |
| 3,798,810 A | 3/1974 | Brisson et al. |
| 3,844,416 A | 10/1974 | Potter |
| 3,865,447 A | 2/1975 | Patterson |
| 3,942,851 A | 3/1976 | Kaplan |
| 3,970,010 A | 7/1976 | Cantley |
| 4,210,802 A | 7/1980 | Sakai |
| 541,111 A | 6/1985 | McDonald |
| 4,653,818 A | 3/1987 | DeBruyn |
| 4,688,026 A | 8/1987 | Scribner et al. |
| 4,737,910 A | 4/1988 | Kimbrow |
| 4,746,830 A | 5/1988 | Holland |
| 4,766,542 A | 8/1988 | Pilarczyk |
| 4,793,495 A | 12/1988 | Preu |
| 4,993,558 A | 2/1991 | Assael |
| 5,047,948 A | 9/1991 | Turner |
| 5,079,006 A | 1/1992 | Urquhart |
| 5,160,048 A | 11/1992 | Leyden et al. |
| 5,208,762 A | 5/1993 | Charhut et al. |
| 5,231,273 A | 7/1993 | Caswell et al. |
| 5,245,163 A | 9/1993 | Bar-Yehuda |
| 5,328,784 A | 7/1994 | Fukuda |
| 5,346,297 A | 9/1994 | Colson et al. |
| 5,389,919 A | 2/1995 | Warren et al. |
| 5,434,775 A | 7/1995 | Sims et al. |
| 5,481,546 A | 1/1996 | Dinkins |
| 5,495,250 A | 2/1996 | Ghaem et al. |
| 5,593,267 A | 1/1997 | McDonald et al. |
| 5,595,356 A | 1/1997 | Kewin |
| 5,597,995 A | 1/1997 | Williams et al. |
| 5,640,002 A | 6/1997 | Ruppert et al. |
| 5,646,389 A | 7/1997 | Bravman et al. |
| 5,646,592 A | 7/1997 | Tuttle |
| 5,689,238 A | 11/1997 | Cannon et al. |
| 5,700,998 A | 12/1997 | Palti |
| 5,771,657 A | 6/1998 | Lasher et al. |
| 5,794,213 A | 8/1998 | Markman |
| 5,797,515 A | 8/1998 | Liff et al. |
| 5,798,693 A | 8/1998 | Engellenner |
| 5,805,456 A | 9/1998 | Higham et al. |
| 5,838,253 A | 11/1998 | Wurz et al. |
| 5,845,264 A | 12/1998 | Nellhaus |
| 5,907,493 A | 5/1999 | Boyer et al. |
| 5,926,093 A | 7/1999 | Bowers et al. |
| 5,936,527 A | 8/1999 | Isaacman et al. |
| 5,963,132 A | 10/1999 | Yoakum |
| 5,974,393 A | 10/1999 | McCullough et al. |
| 5,996,889 A | 12/1999 | Fuchs et al. |
| 6,008,727 A | 12/1999 | Want et al. |
| 6,021,392 A | 2/2000 | Lester et al. |
| 6,057,756 A | 5/2000 | Engellenner |
| 6,057,764 A * | 5/2000 | Williams .................. 340/572.1 |
| 6,098,892 A | 8/2000 | Peoples |
| 6,116,505 A | 9/2000 | Withrow |
| 6,150,942 A | 11/2000 | O'Brien |
| 6,170,746 B1 | 1/2001 | Brook et al. |
| 6,202,923 B1 | 3/2001 | Boyer et al. |
| 6,209,978 B1 | 4/2001 | Khan |
| 6,219,587 B1 | 4/2001 | Ahlin et al. |
| 6,223,137 B1 | 4/2001 | McCay et al. |
| 6,232,876 B1 | 5/2001 | Maloney |
| 6,245,057 B1 | 6/2001 | Sieben et al. |
| 6,249,212 B1 | 6/2001 | Beigel et al. |
| 6,259,654 B1 | 7/2001 | de la Huerga |
| 6,294,999 B1 | 9/2001 | Yarin et al. |
| 6,318,536 B1 | 11/2001 | Korman et al. |
| 6,324,522 B2 | 11/2001 | Peterson et al. |
| 6,339,732 B1 | 1/2002 | Phoon et al. |
| 6,354,493 B1 | 3/2002 | Mon |
| 6,357,662 B1 | 3/2002 | Helton et al. |
| 6,366,206 B1 | 4/2002 | Ishikawa et al. |
| 6,366,220 B1 | 4/2002 | Elliott |
| 6,380,858 B1 | 4/2002 | Yarin et al. |
| 6,392,544 B1 | 5/2002 | Collins et al. |
| 6,415,295 B1 | 7/2002 | Feinberg |
| 6,415,978 B1 | 7/2002 | McAllister |
| 6,430,268 B1 | 8/2002 | Petite |
| 6,440,069 B1 | 8/2002 | Raymond et al. |
| 6,448,886 B2 | 9/2002 | Garber et al. |
| 6,450,406 B2 | 9/2002 | Brown |
| 6,464,142 B1 | 10/2002 | Denenberg et al. |
| 6,496,806 B1 | 12/2002 | Horwitz et al. |
| 6,502,005 B1 | 12/2002 | Wrubel et al. |
| 6,522,945 B2 | 2/2003 | Sleep et al. |
| 6,529,786 B1 | 3/2003 | Sim |
| 6,557,758 B1 | 5/2003 | Monico |
| 6,564,121 B1 | 5/2003 | Wallace et al. |
| 6,611,806 B1 | 8/2003 | Harvey |
| 6,648,153 B2 | 11/2003 | Holmes |
| 6,714,121 B1 | 3/2004 | Moore |
| 6,758,403 B1 | 7/2004 | Keys et al. |
| 6,763,996 B2 | 7/2004 | Rakers et al. |
| 6,769,228 B1 | 8/2004 | Mahar |
| 6,877,658 B2 | 4/2005 | Raistrick et al. |
| 6,935,560 B2 * | 8/2005 | Andreasson et al. ......... 235/385 |
| 6,995,675 B2 | 2/2006 | Curkendall et al. |
| 7,142,118 B2 | 11/2006 | Hamilton et al. |
| 7,148,803 B2 | 12/2006 | Bandy et al. |
| 7,158,030 B2 * | 1/2007 | Chung ...................... 340/572.1 |
| 7,175,081 B2 | 2/2007 | Andreasson et al. |
| 7,289,015 B2 | 10/2007 | Moyer |
| 7,382,263 B2 | 6/2008 | Danowski et al. |
| 7,672,859 B1 | 3/2010 | Louie et al. |
| 2001/0017817 A1 | 8/2001 | de la Huerga |
| 2001/0040512 A1 | 11/2001 | Hines et al. |
| 2002/0132226 A1 | 9/2002 | Nair et al. |
| 2002/0180588 A1 | 12/2002 | Erickson et al. |
| 2003/0086338 A1 | 5/2003 | Sastry et al. |
| 2003/0191430 A1 | 10/2003 | D'Andrea et al. |
| 2003/0200726 A1 | 10/2003 | Rast |
| 2004/0036623 A1 | 2/2004 | Chung |
| 2005/0237201 A1 | 10/2005 | Nedblake |
| 2006/0190628 A1 | 8/2006 | Linton et al. |

FOREIGN PATENT DOCUMENTS

| | | |
|---|---|---|
| EP | 1 049 042 | 11/2000 |

OTHER PUBLICATIONS

Derfler, Frank J. et al., How Networks Work, Millenium Ed., Que Corporation, Aug. 23, 2000.
Gralla, Preston, How the Internet Works, Millenium Ed., Que Corporation, Sep. 23, 1999.
Final Office action dated Feb. 23, 2005, U.S. Appl. No. 09/991,530, filed Aug. 18, 2002.
Office action dated Oct. 13, 2004, U.S. Appl. No. 10/223,336, filed Aug. 18, 2002.
Final Office action dated Jun. 23, 2005, U.S. Appl. No. 10/223,336, filed Aug. 18, 2002.
Office action dated Aug. 15, 2006, U.S. Appl. No. 10/223,336, filed Aug. 18, 2002.
Final Office action dated Apr. 25, 2007, U.S. Appl. No. 10/223,336, filed Aug. 18, 2002.
Office action dated Aug. 1, 2011, U.S. Appl. No. 12/715,256, filed Mar. 1, 2010.
Office action dated Aug. 7, 2008, U.S. Appl. No. 10/928,756, filed Aug. 26, 2004.
Final Office action dated Jun. 18, 2009, U.S. Appl. No. 10/928,756, filed Aug. 26, 2004.
Office action dated Jan. 19, 2010, U.S. Appl. No. 12/268,389, filed Nov. 10, 2008.
Final Office action dated Oct. 4, 2010, U.S. Appl. No. 12/268,389, filed Nov. 10, 2008.
Advisory Action dated May 13, 2010, U.S. Appl. No. 12/268,389, filed Nov. 10, 2008.

Office action dated Dec. 23, 2003, U.S. Appl. No. 10/223,308, filed Aug. 18, 2002.
Final Office action dated Oct. 8, 2004, U.S. Appl. No. 10/223,308, filed Aug. 18, 2002.
Office action dated Dec. 2, 2005, U.S. Appl. No. 10/223,308, filed Aug. 18, 2002.
Final Office action dated Aug. 25, 2006, U.S. Appl. No. 10/223,308, filed Aug. 18, 2002.
Office action dated Nov. 2, 2007, U.S. Appl. No. 10/223,308, filed Aug. 18, 2002.
Final Office action dated Dec. 24, 2008, U.S. Appl. No. 10/223,308, filed Aug. 18, 2002.
Office action dated Mar. 2, 2010, U.S. Appl. No. 10/223,308, filed Aug. 18, 2002.
Office action dated Jun. 9, 2011, U.S. Appl. No. 12/825,020, filed Jun. 28, 2010.
Office action dated Jun. 11, 2009, U.S. Appl. No. 09/715,439, filed Nov. 16, 2000.
Office action dated Nov. 27, 2007, U.S. Appl. No. 09/715,439, filed Nov. 16, 2000.
Office action dated Nov. 6, 2006, U.S. Appl. No. 09/715,439, filed Nov. 16, 2000.
Office action dated Jan. 12, 2005, U.S. Appl. No. 09/715,439, filed Nov. 16, 2000.
Office action dated Mar. 30, 2004, U.S. Appl. No. 09/715,439, filed Nov. 16, 2000.
Office action dated Sep. 5, 2003, U.S. Appl. No. 09/715,439, filed Nov. 16, 2000.
Office action dated Oct. 21, 2002, U.S. Appl. No. 09/715,439, filed Nov. 16, 2000.
Final Office action dated Sep. 4, 2008, U.S. Appl. No. 09/715,439, filed Nov. 16, 2000.
Final Office action dated Jun. 15, 2007, U.S. Appl. No. 09/715,439, filed Nov. 16, 2000.
Final Office action dated Sep. 21, 2005, U.S. Appl. No. 09/715,439, filed Nov. 16, 2000.
Final Office action dated May 15, 2003, U.S. Appl. No. 09/715,439, filed Nov. 16, 2000.
Final Office action dated Jul. 16, 2004, U.S. Appl. No. 09/829,536, filed Apr. 9, 2001.
Final Office action dated Dec. 28, 2005, U.S. Appl. No. 09/829,536, filed Apr. 9, 2001.
Final Office action dated Dec. 4, 2007, U.S. Appl. No. 09/829,536, filed Apr. 9, 2001.
Office action dated Nov. 12, 2003, U.S. Appl. No. 09/829,536, filed Apr. 9, 2001.
Office action dated Apr. 8, 2005, U.S. Appl. No. 09/829,536, filed Apr. 9, 2001.
Office action dated Apr. 19, 2007, U.S. Appl. No. 09/829,536, filed Apr. 9, 2001.
Office action dated Apr. 28, 2004, U.S. Appl. No. 09/991,249, filed Nov. 16, 2001.
Final Office action dated May 17, 2006, U.S. Appl. No. 09/991,249, filed Nov. 16, 2001.
Office action dated Sep. 8, 2004 U.S. Appl. No. 09/991,529, filed Nov. 16, 2001.
Final Office action dated Feb. 21, 2007, U.S. Appl. No. 09/991,529, filed Nov. 16, 2001.
Office action dated Mar. 13, 2009 U.S. Appl. No. 10/929,110, filed Aug. 26, 2004.
Office action dated Jan. 14, 2008 U.S. Appl. No. 10/928,717, filed Aug. 26, 2004.
Office action dated Apr. 4, 2007, U.S. Appl. No. 11/213,321, filed Aug. 25, 2005.
Office action dated Dec. 17, 2007, U.S. Appl. No. 11/213,321, filed Aug. 25, 2005.
Office action dated May 10, 2004, U.S. Appl. No. 09/991,530, filed Aug. 18, 2002.
Office action dated Feb. 15, 2012, U.S. Appl. No. 12/715,256, filed Mar. 1, 2010.

* cited by examiner

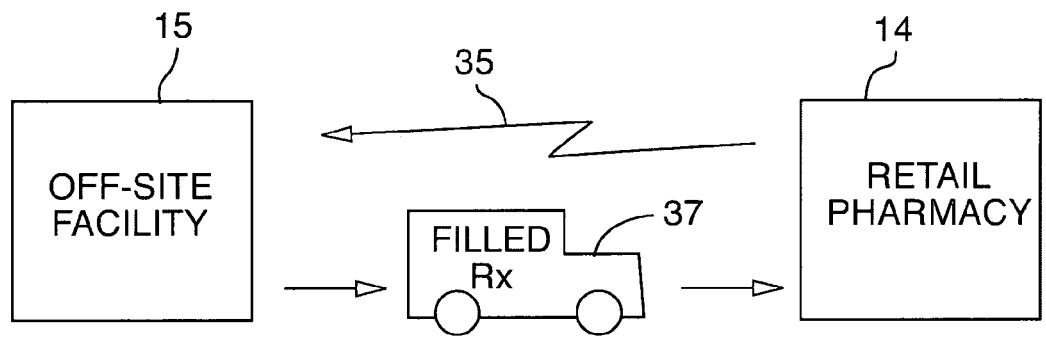
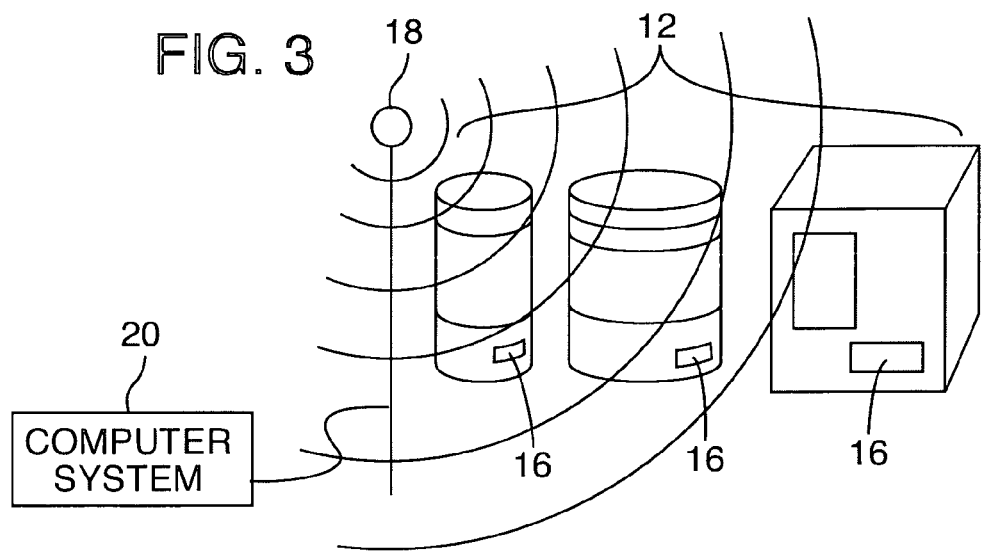

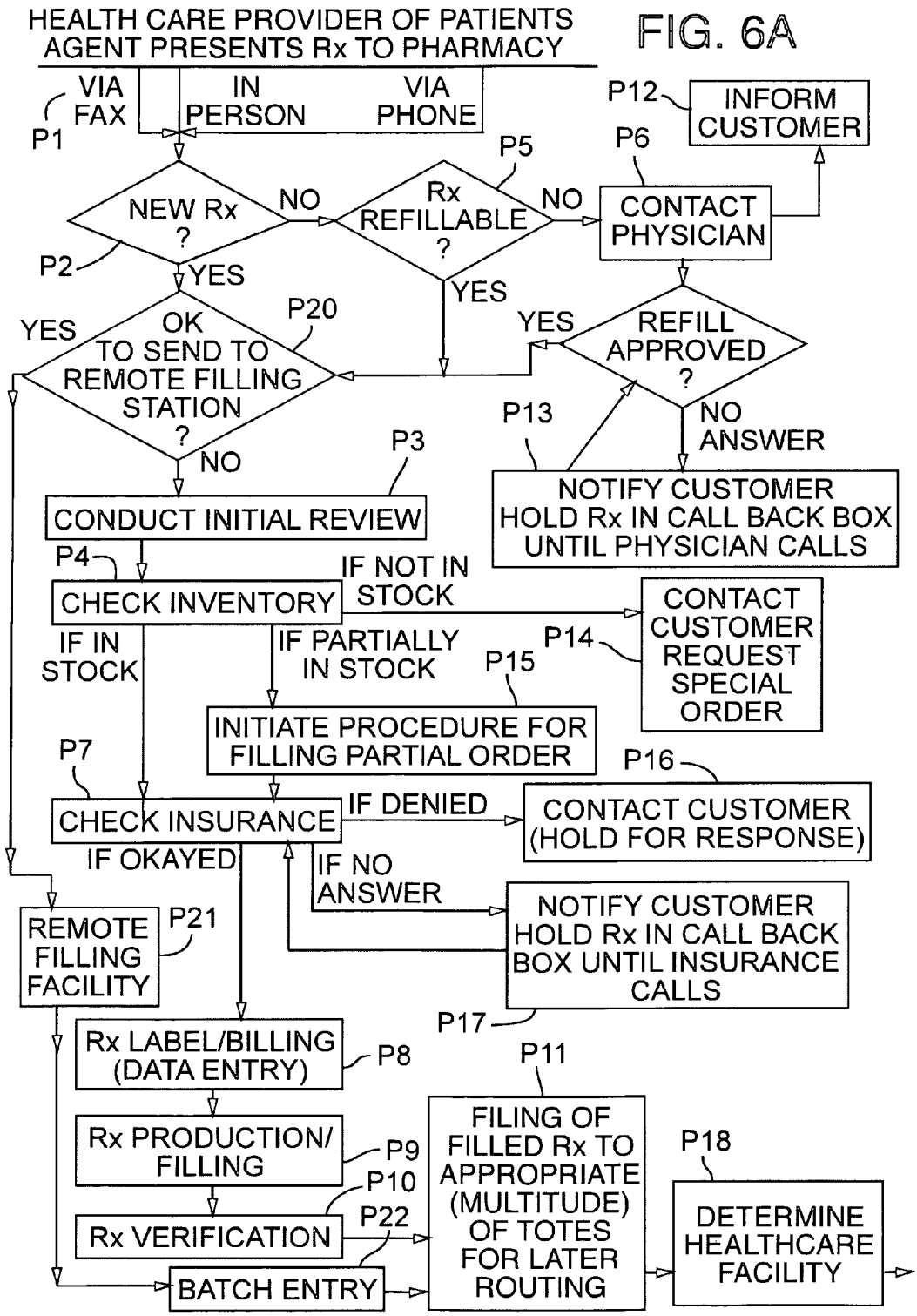

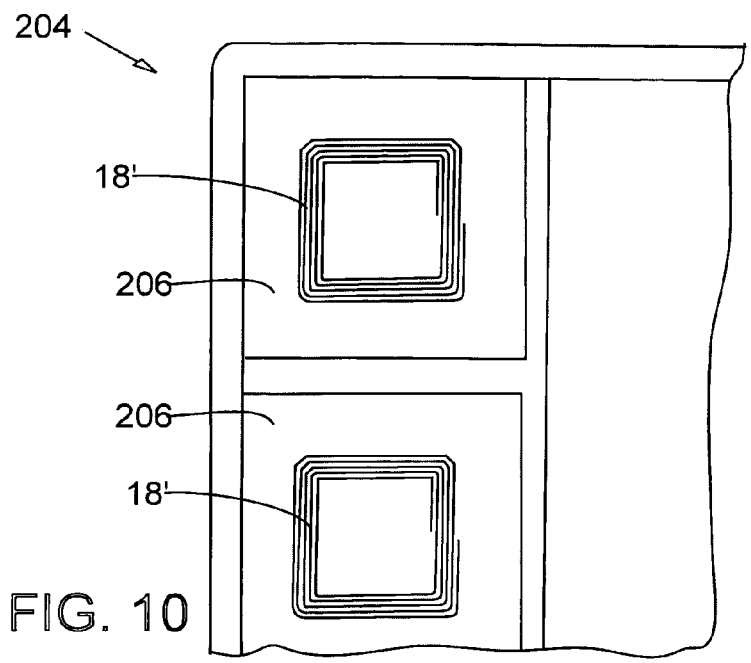
FIG. 10
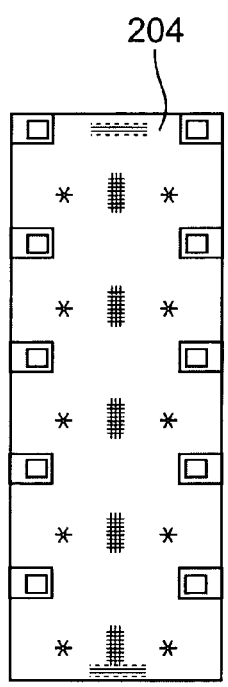  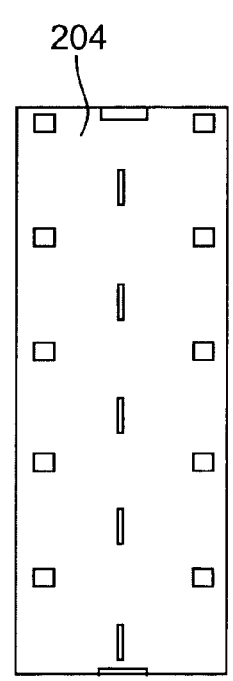
FIG. 11A   FIG. 11B   FIG. 11C

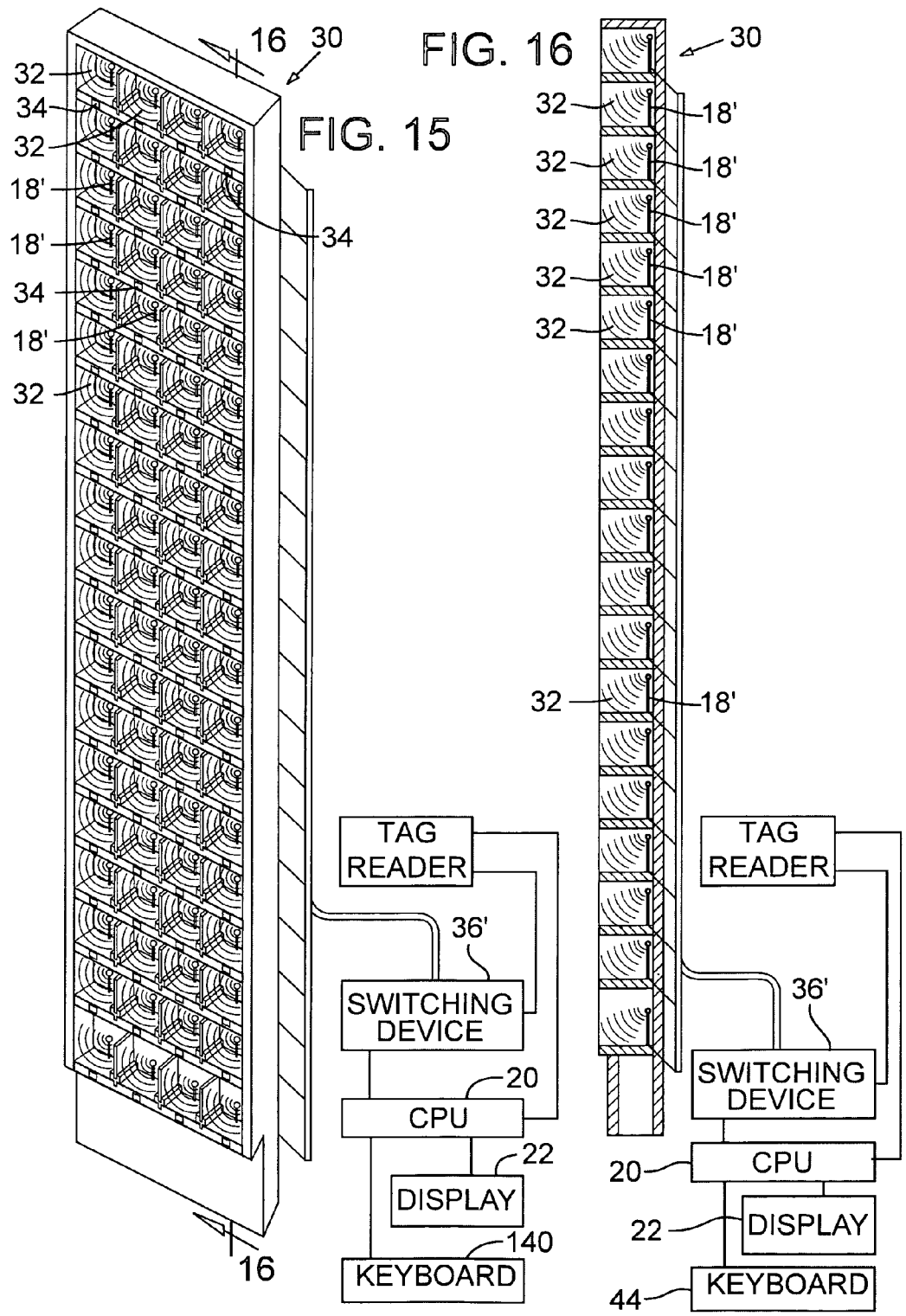

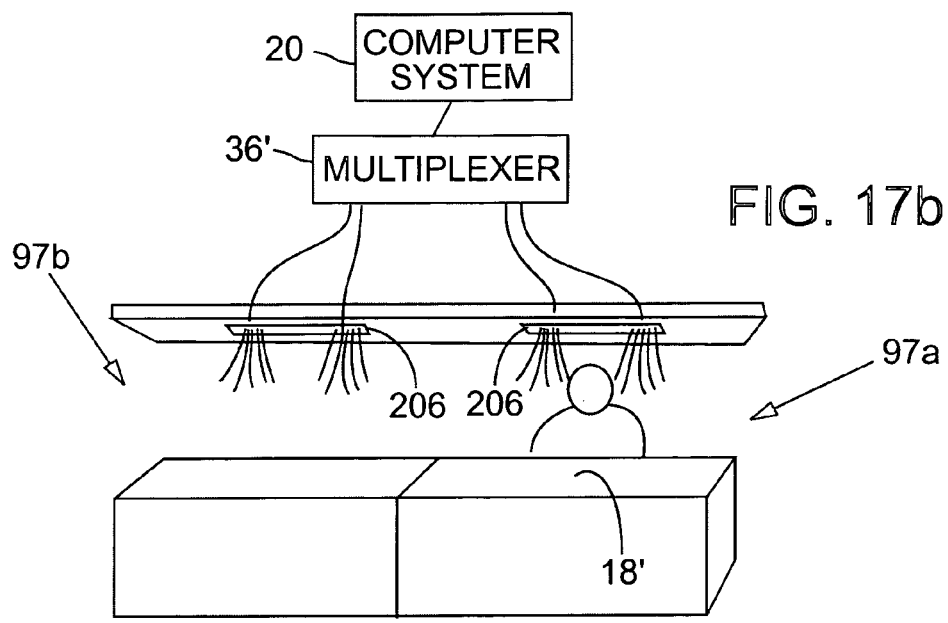
FIG. 17b
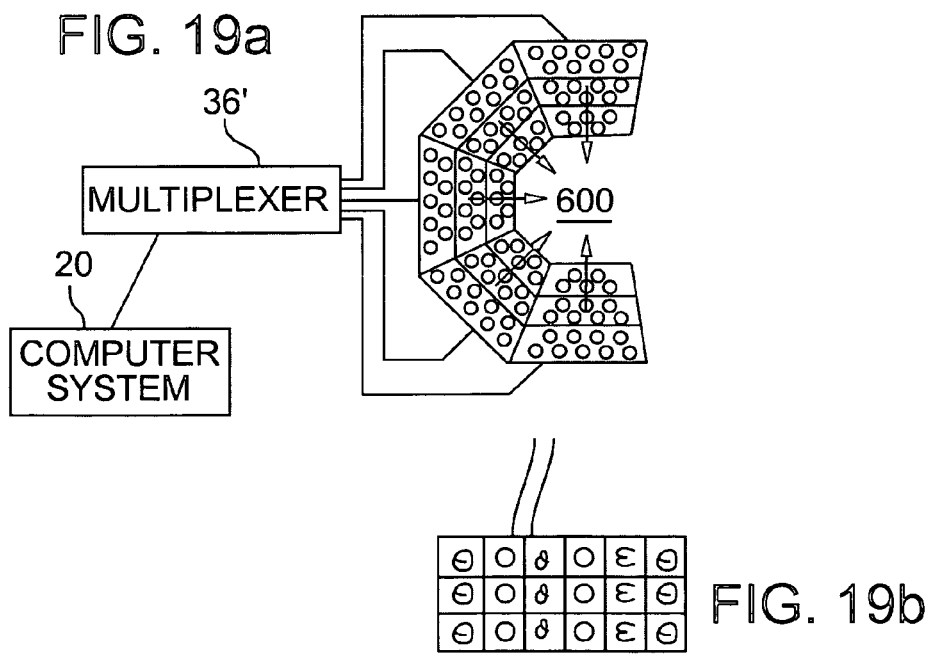
FIG. 19a
FIG. 19b

PORTABLE PRESCRIPTION ORDER DISTRIBUTION CART AND TRACKING SYSTEM

This application is a continuation-in-part of U.S. patent application Ser. No. 09/715,439, filed on Nov. 16, 2000, now U.S. Pat. No. 7,672,859; Ser. No. 09/829,536, filed on Apr. 9, 2001, now abandoned; Ser. No. 09/991,529, filed on Nov. 16, 2001, now U.S. Pat. No. 7,496,521; Ser. No. 09/991,249, filed on Nov. 16, 2001, now abandoned; Ser. No. 09/991,530, filed on Nov. 16, 2001, now abandoned; Ser. No. 10/223,336, filed on Aug. 18, 2002, now abandoned; and Ser. No. 10/223,308, filed on Aug. 18, 2002 now U.S. Pat. No. 7,887,146, and Ser. No. 10/925,360, filed on Aug. 23, 2004, now abandoned, the disclosures of which are hereby incorporated by reference. This application also claims priority to U.S. Provisional Patent Application Ser. No. 60/496,829 filed on Aug. 21, 2003.

FIELD OF THE INVENTION

The present invention relates to a portable prescription order distribution cart and a related tracking system that automatically detects and tracks the prescription order during the distribution process, such as delivery from a remote pharmacy to a medical or other health care facility and ultimate distribution to a patient or the like.

BACKGROUND OF THE INVENTION

Pharmaceutical medications increase the lives and the quality of lives of millions of people. Moreover, as the general population ages and new beneficial drugs are introduced, prescription order volumes to be filled at pharmacies and distributed to individual customers and through health care providers such as hospitals, convalescent centers, and the like, are expected to double within the next few years. This present and expected increase in order volume places enormous pressure on pharmacists, other pharmacy workers, and health care providers, who strive to fill and distribute each order efficiently, accurately and quickly.

The process of retrieving, filling, and distributing a prescription order to a patient or customer can include many different people and organizations performing numerous tasks. An error with any one of these tasks can lead to the mishandling of a patient's prescription order. Such mishandling of a prescription order often results in a patient not timely receiving their prescription order or receiving a wrong, possibly even deadly, prescription order or the like.

For example, a healthcare facility such as a convalescent center, elder care residential facility, manages care facility, hospital, and the like, must regularly distribute thousands of prescription medications to hundreds of its residents each week. This process usually includes sending the resident's prescription orders to a remote, off-site, pharmacy, then receiving the filled prescription orders back from the pharmacy for distribution. The filled prescription orders are then typically separated and individually identified for each resident. Usually, the separated prescription orders are then placed in a portable cart for distribution.

A worker then moves the portable cart from room to room through the convalescent center or elder care residential facility and distributes each resident's prescription orders to the appropriate resident. The worker also usually maintains a written record of which medications have been administered to which residents.

In order to operate effectively, such distribution systems require workers with acute attention to detail skills, a high degree of competence, and a desire to consistently perform these types of repetitive tasks with great accuracy. Unfortunately, the supply of such workers is often not able to keep up with the demand. Moreover, as economic demands on these types of facilities increase, many such facilities may seek to reduce their costs by hiring less skilled and less costly workers to perform these tasks.

Recently, efforts have been made to reduce the likelihood of a worker accidentally delivering the wrong prescription order to a patient. However, such systems still require the worker to perform some sort of affirmative act, such as pressing a button or operating a scanning device, to update the tracking system with relevant information. Accordingly, since the worker remains critical to the effective operation of the system, human error continues to be a major factor associated with improper distribution of prescription medications.

SUMMARY OF THE INVENTION

Despite the known portable prescription order tracking and distribution systems, there remains a need for an economical, portable prescription order tracking and distribution system that automatically detects the presence of a particular patient or customer's prescription order and automatically tracks its distribution to a particular customer. In addition to other benefits that will become apparent in the following disclosure, the present invention fulfills these needs.

The present invention is a portable cart and related system for operating the cart to automatically detect and track a prescription order through distribution. In a preferred embodiment the system also detects the worker and the patient or customer receiving the prescription order and uses this information along with the detected prescription order to verify the proper distribution of the prescription order to the correct patient. More preferably, the system also records, or charts, the distribution event.

One such system includes using tags, such as Radio-Frequency Identification ("RFID") tags, and their related readers to locate objects through electromagnetic interrogation of a spatial region to determine the presence of an object within that special region. A unique tag is operably secured to each prescription order, and tag readers, which are in communication with a computer system, are positioned near the cart and, if needed, throughout the facility, to detect the presence of a tag within a defined physical location. Preferably, unique tags are also operably secured to each worker and patient. Accordingly, the computer system correlates the prescription orders, patient, and worker information to determine if a particular patient has been given their prescription order, if the correct prescription order was distributed, and which worker administered it.

Preferably, the cart includes a plurality of cubbies therein, with each cubby having its own tag reader. More preferably, the tag reader, which is in communication with a computer system, is operably secured to a multiplexer with a plurality of antennae extending therefrom. Each antenna is positioned at a particular cubby location. The multiplexer cycles through connecting each antenna such that all locations are scanned using the common tag reader.

Preferably, in situations where the antenna are in close proximity to each other, such as being in adjacent cubbies in the cart, the antenna signals are shielded from each other, say for example, with a grounding circuit positioned therebetween. More preferably, the antennas are formed onto a substantially planar frame with a grounding circuit extending therearound, thereby directing the tag reading signal substantially perpendicular to the planar frame. Accordingly, the planar frame containing the antenna may be positioned substantially vertically adjacent to a storage bin in a will call storage area, or positioned substantially horizontally under a worker's work area. Accordingly, the detectable field provided by the antenna can be limited to a very specific physical area within a work area filled with other tracked work areas positioned in very close proximity.

Additional objects and advantages of the present invention will be apparent from the detailed description of the preferred embodiment thereof, which proceeds with reference to the accompanying drawings.

BRIEF DESCRIPTION OF THE DRAWINGS

FIG. 2 is a schematic diagram of an exemplar retail pharmacy using a remote filling station to fill one or more prescription orders, and return the filled prescriptions to the retail pharmacy for distribution.

FIG. 3 is an isometric view of simultaneous scanning of a plurality of prescription orders in accordance with an embodiment of the present invention.

FIG. 10 is a top plan view of an exemplar, planar, antenna array card showing possible shielding encircling each antenna.

FIG. 11 is a top, side, and back view of the antenna array card of FIG. 10.

FIG. 15 is a front, isometric view of the storage structure of FIG. 14 showing a possible connection to a computing device.

FIG. 16 is a side view of the storage structure of FIG. 15.

FIG. 17b is an alternative exemplar, isometric view of a possible workstation having a substantially horizontally mounted planar frame containing at least one tag reader antenna therein.

FIG. 18 is a top view of the workstation of FIG. 17a.

FIG. 19a is a top view of an exemplar array of tag reading antenna directed to define a common scanning space or scanning tunnel.

FIG. 19b is a side view of an alternative exemplar array of tag reading antenna directed to define a common scanning space or scanning tunnel.

DETAILED DESCRIPTION OF PREFERRED EMBODIMENTS

A prescription order 12 tracking and distribution system 10 that uses a portable cart 11 (FIGS. 20 & 21) having a plurality of individually-identified cubbies therein is disclosed in FIGS. 1-24.

Figure 5:
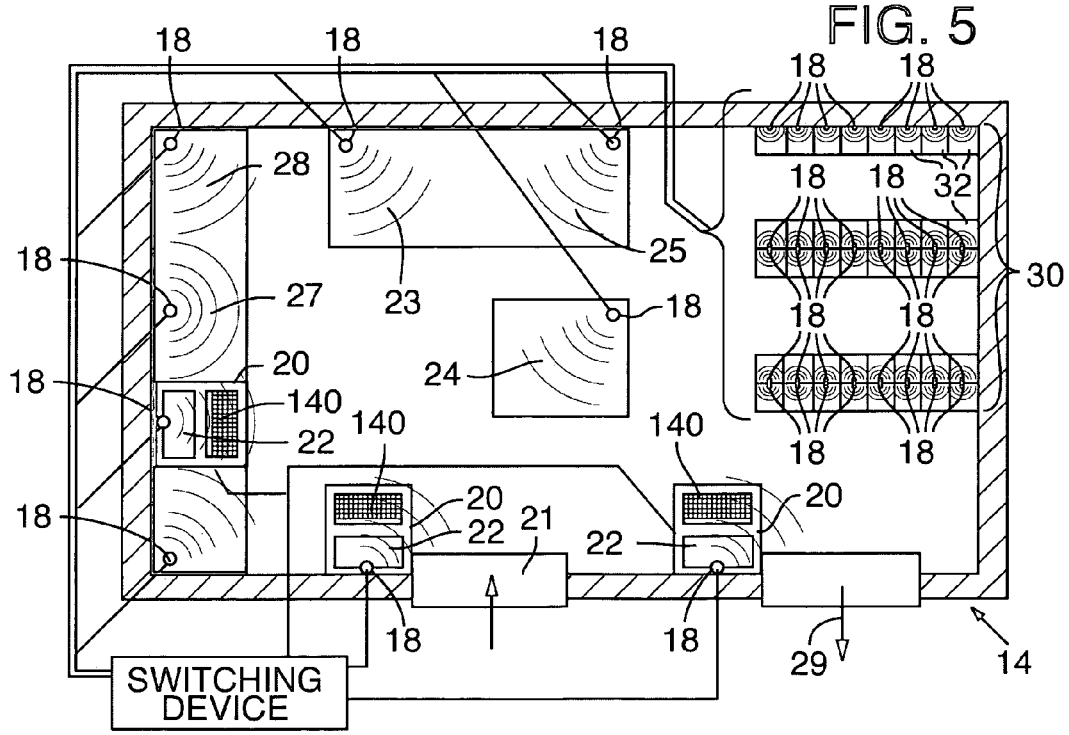
FIG. 5 is a schematic view of a prescription order tracking system used in a remote pharmacy in accordance with a preferred embodiment of the present invention.
Figure 6A:
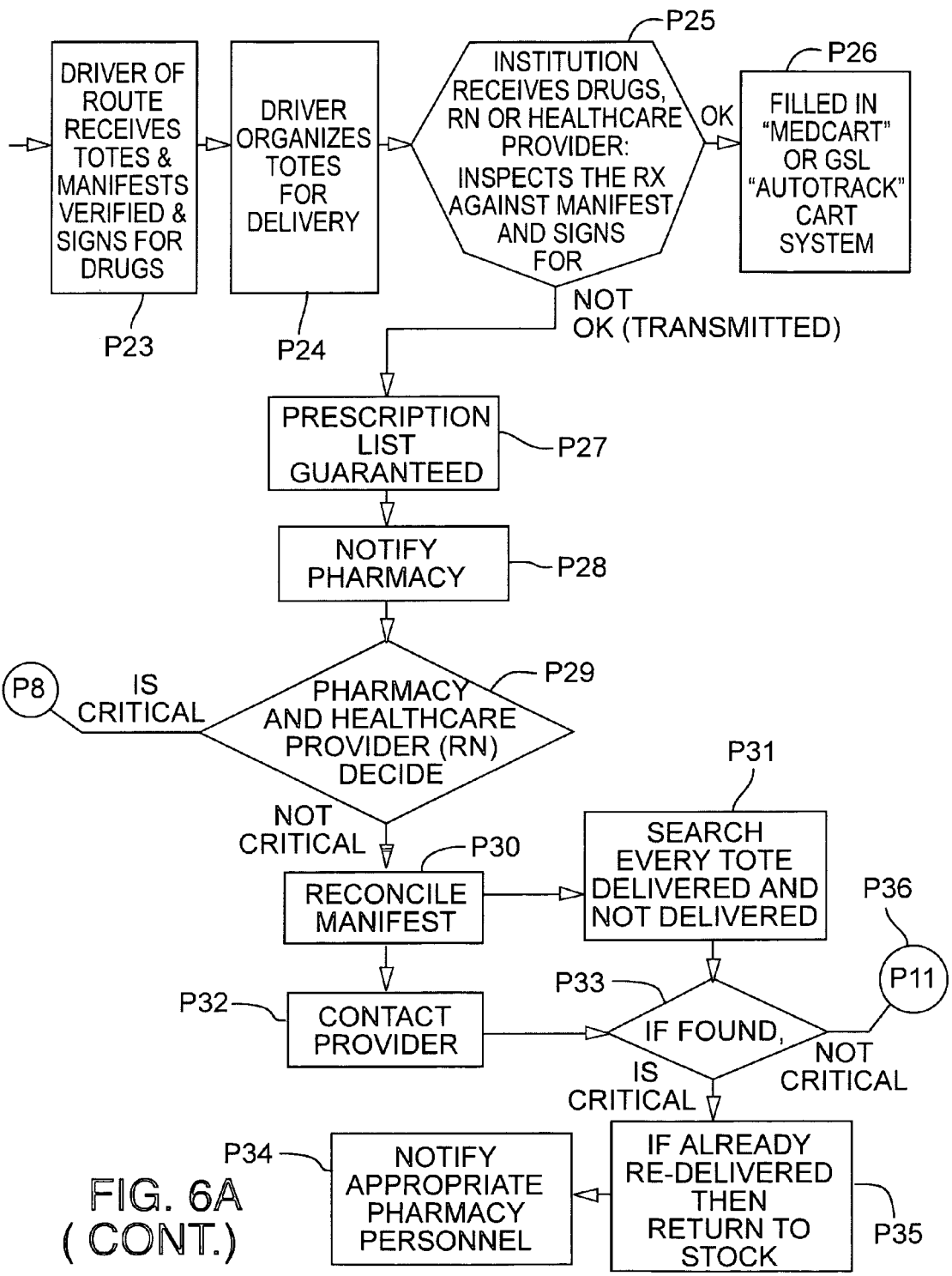
FIG. 6A is a block diagram of an exemplar health care provider prescription order filling system showing a possible remote pharmacy filling process.

In general and as shown in FIGS. 5, 6A, 6B, and 20, a prescription order 12 is presented to the remote pharmacy 14 by a healthcare provider or other agent (hereafter collectively referred to as a "healthcare provider") for a patient. Referring to FIG. 6A, the remote pharmacy or the healthcare provider assigns an identification tag 16 to the prescription order 12. Tag reading devices 18 are positioned at key locations throughout the pharmacy 14 (FIG. 5) and the healthcare provider's facility 17 (FIG. 21) and in communication with a computer system 20 having a display 22, such that the movement of the prescription order 12 throughout the pharmacy 14 and/or the healthcare provider's facility 17 automatically detects and records the location of the tag 16 without further worker input. A plurality of tags may be simultaneously tracked, thereby facilitation bulk processing and distribution of prescription orders, particularly those received from the off-site facility 15. Moreover, each tag preferably includes read-writable memory that is preferably coded with key information about the prescription order, such as the customer's name, identifying information, date of birth, social security number, prescribed drug, insurance information, directions for use, National Drug Control ("NDC") number, and the like. Accordingly, a pharmacy worker within the pharmacy, a worker at the healthcare provider's facility or even a worker at a third remote location can quickly and easily determine all relevant information about a particular prescription order without necessarily having to first correlate a tag identification code with a computer system database.

In addition, a worker can easily determine the location of the prescription order 12 within the pharmacy and/or the healthcare provider's facility 17 by entering commands in the computer system 20 with a user input device such as a keyboard 120 to display the location of the prescription order 12 on the computer display 22. The individual elements forming the present invention are discussed in greater detail below.

A. Tags with Read-Writable Memory

Preferably, one or more readers 18 locate tags 16 through electromagnetic interrogation of a spatial region to determine the presence of an object. One such system is disclosed in U.S. Pat. No. 6,057,756 to Engellenner, the disclosure of which is hereby incorporated by reference. In general, the tag 16 is an electromagnetic antenna and/or signal receiver which responds either passively or actively to announce the presence (or absence) of an object within a controlled region defined by a broadcasted electromagnetic interrogation signal. Preferably, each tag 16 includes a coding mechanism for uniquely identifying it with respect to other tags in the system.

Figure 1:
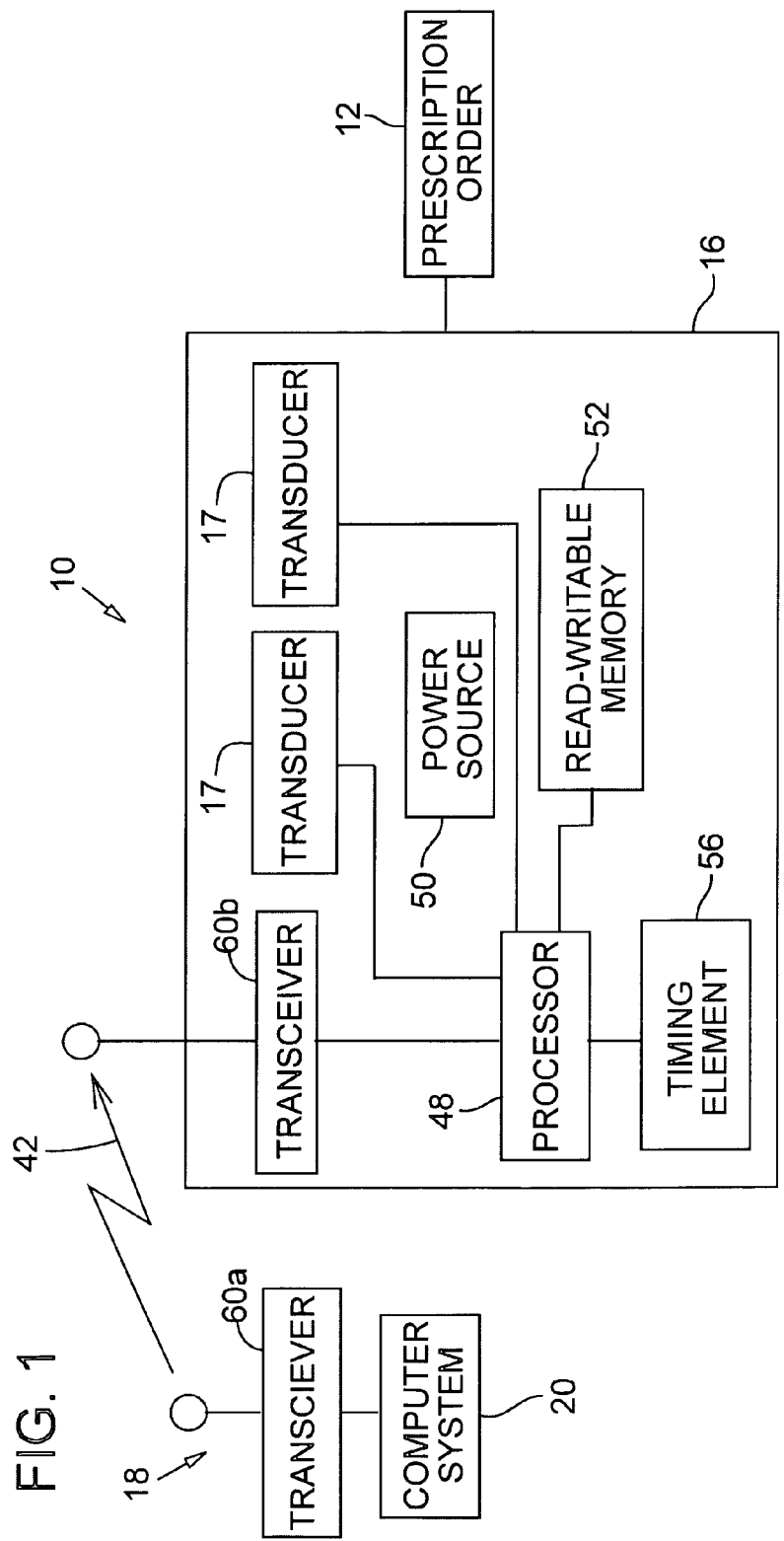
FIG. 1 is a schematic diagram of an identification tag in accordance with an embodiment of the present invention.

FIG. 1 discloses an exemplar tag 16 and related components for locating a prescription order 12 in a pharmacy 14. The computer system 20 is operably connected to a transceiver 60*a*, such as for example, a conventional Radio-Frequency Identification ("RFID") tag, that transmits a signal 42 to a plurality of tags 16. Each tag 16 is assigned to travel with a unique prescription order 12, and includes a transceiver 60*b* for receiving the signal and internal circuitry such as a processor 48, power source 50 and memory 52 which contains a unique identifier for that tag and control logic to preferably activate one or more transducers 17, which serve as the worker signaling device when the tag 16 receiving a unique signal 42 from the transmitter 40. Such transducers 17 may also be operably secured to the tag reader 18 or some other structure as needed to assist a worker.

Figure 4:
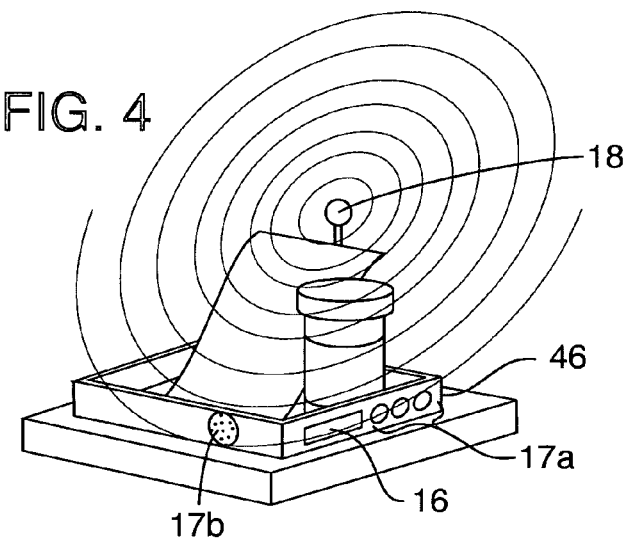
FIG. 4 is an isometric view of a prescription order having a tag operably secured thereto with the tag having a plurality of transducers thereon.

Preferably, the transducer 17 are either a light 17*a* (FIG. 4) or audio speaker 17*b* (FIG. 4). More preferably, there are a plurality of transducers 17 that can be individually activated on each tag 16. For example, there can be three lights of different colors (i.e. red, yellow, and green), which can be activated either alone or in combination to identify the status of that prescription order 12, with a different status being denoted by a different transducer being activated.

More preferably, the memory 52 on the tag is read-writable that is preferably coded with key information about the prescription order, such as the customer's name, identifying information, date of birth, social securing number, prescription number, proper storage instructions, known side-effects, expiration date, prescribed drug, insurance information, directions for use, National Drug Control ("NDC") number, and the like.

The computer system 20 includes appropriate application programs 136 (FIG. 7) and memory 122 (FIG. 7) to correlate a customer's identifying information such as their name, phone number, date of birth, social security number, and the like, with the unique identifier and/or other information such as the desired destination of the prescription order, travel history, and the like in the memory of the tag traveling with that prescription order. Accordingly, when a pharmacy worker wishes to locate a customer's prescription order, he or she may find the customer's identifying information on the computer system 20, and cause the computer system to transmit the unique signal 42 through the transceiver 60*a* to wirelessly activate one or more transducers 17 on the tag 16 associated with the customer's prescription order 12. For example, the tag's audio speaker 17*b* may make an audible sound, or one or more lights 17*a* on the tag 16 may light and/or blink.

Preferably, a plurality of fixed or handheld transceivers, which are collectively referred to as tag readers 18 herein, are spaced apart from each other and positioned at desired locations within the pharmacy 14 to define spaced-apart interrogation zones within the pharmacy. Each tag reader 18 includes a front-end transmitter 62 that generates a digitally encoded signal 64. Preferably, the signal 64 is chosen to facilitate a response from only one uniquely coded tag 16. The receiver portion 66 of the tag reader 18 can induce a coded signal detector that senses the transponder signal 64 and correlates it with a stored code to identify that the tag 16 is present in a particular interrogation zone, thereby also determining the tag's location within the pharmacy.

The computer system 20 can also use conventional triangulation techniques to determine the location of the tag within the pharmacy. In which case, only two spaced-apart tag readers 18 need be placed within the pharmacy. Alternatively, using quasi-sonar-type locating techniques, a single tag reader 18 could be used determine the location of the tag within the pharmacy.

Each tag 16 can be either passive or active. In the passive mode, the tag circuitry accumulates and then returns a signal, if the interrogation signal matches a predefined code sequence stored in memory in the tag's circuitry. In an active mode, each tag further includes a power source 50 that assists with signal amplification, detection and/or wave forming.

B. Prescription Order Tracking

Tags 16 may also be used to track the location of the prescription order as it travels throughout the off-site pharmacy 14 an off-site prescription filling center 15 and/or a healthcare facility 17. For example and referring to FIG. 5, a prescription order 12 is presented to the pharmacy 14 and assigned an identification tag 16 with one or more transducers 17 thereon. Tag readers 18 are positioned at key locations throughout the pharmacy 14 and in communication with the computer system 20 having a display 22, such that the movement of the prescription order 12 throughout the pharmacy 14 automatically detects and records the location of the tag 16 without further worker input. In addition to, or alternatively, the transducers 17 can be operably secured to a tag reader 18 or some other object.

Accordingly, a worker can easily determine the location of the prescription order 12 within the pharmacy by entering commands in the computer system 20 with a user input device such as a keyboard 120 to display the location of the prescription order 12 on the computer display 22. Alternatively, the computer system can detect the identity of a customer based on predetermined criteria such as by detecting a tag operably secured to the customer, or through bio-medical detection techniques such a retina or fingerprint scanning, and initiating retrieval of the detected customer's prescription order.

Each tag reader 18 is placed in communication with the computer system such that information regarding the customer, his prescription order position, and the status of his order can be readily displayed on the computer display 22, and thereby facilitating location of the prescription order 10 within the pharmacy 14.

Preferably, the identification tags 16 are attached to the prescription label, detachably secured to the prescription order, or rigidly secured to a carrier 46 (FIG. 4) containing these documents and other materials related to filling the prescription. The tags themselves can be either rigidly or detachably secured to the prescription order. For example, the tags can be directly secured to the prescription with adhesive or secured within a prescription lid. Also, the tags can be secured to a fastener, such as a paperclip, that is detachably secured to the prescription order.

1. Pharmacy Prescription Order Filling Procedure

Referring specifically to FIG. 6A, an exemplary pharmacy, which is preferably a remote pharmacy for filling prescription orders for a healthcare facility 17 (FIG. 17) prescription order filling procedure is disclosed. In step P1, the healthcare facility presents a prescription order, which could include a written prescription form, a renewable prescription label, or any other tangible medium documenting a request for a prescription by a health care provider is presented to the pharmacy either in person, via facsimile, via phone, or via a computer transmission, such as e-mail. A pharmacy worker then reviews the prescription order and attaches a unique tag 16 (FIG. 4) to it that is readable by a tag reader 18 (FIG. 4) to determine its location within the pharmacy 14.

As shown in Step P2, the pharmacy worker then determines if the prescription order is for a new prescription. If not, the worker determines if the prescription is refillable (Step P5). If the prescription is not refillable, the pharmacy worker will typically contact the physician or the physician's office to determine if the prescription should be refilled (Step P6). If the physician denies a refill, the customer is informed (Step P12). If the physician does not answer the customer is notified and the pharmacy typically holds the prescription order until the physician calls back (Step P13).

If the pharmacy worker ultimately determines that the prescription order is fillable, by the answers to any of Steps P2, P5, or P6 being affirmative, the pharmacy worker then must typically determines if the prescription order is able to be sent to a remote filling facility or if it will be filled onsite within the pharmacy itself (Step P20).

A. Onsite Filling of Prescription Order

If the pharmacy worker determines that the prescription order is to be filled onsite, he or she first conducts an initial review (Step P3) which includes checking the available inventory for the prescribed drug (Step P4), determining if there is available insurance (Step P7) and if required, obtaining approval from the insurer and preparing the label and necessary billing and information disclosure paperwork (Step P8).

Regarding Step P4, if the inventory is not in stock, the pharmacy worker typically informs the customer and offers the customer an opportunity to special order the prescribed drug (Step P14). If there is only a partial amount of the prescribed drug in stock, the pharmacy worker will typically initiate a procedure for filling only a partial order (Step P15). This procedure typically includes preparing additional paperwork to alert the customer that only a partial order has been filled, and ordering additional quantities of the prescribed drug.

Regarding Step P7, if the insurance coverage is denied, the prescription order is typically held in an area pending the customer being contacted to request authorization to proceed (Step P16). If the insurer cannot be contacted, the pharmacy has the option to either fill the prescription and alert the customer upon pick-up, or hold the prescription order pending a response from the insurer (Step P17).

After the initial review is complete, the prescription order and related paperwork is presented to a technician for data entry (Step P8) and filling (Step P9), the technician fills the prescription order and attaches the label. The technician then presents the filled prescription order and related paperwork to a registered pharmacist for verification (Step P10).

Following verification, the filled prescription is placed in a storage area pending delivery to the healthcare facility (Step P11). Usually, the remote pharmacy fills prescription orders for several different healthcare facilities. Each healthcare facility usually has many patients needing prescription orders therein, and the remote pharmacy often fills a plurality of prescription orders for each patient. In such case, these orders for patients within each healthcare facility are grouped together in a common tote or the like, so that all the filled prescriptions for patients in a common healthcare facility may be transported to that facility in the same shipment or delivery run.

Preferably, the totes are delivered to the healthcare provider by a courier, such as a driver or the like as shown in step P23. In such case, the driver receives the totes and a related manifest of the prescription orders and their related patient identifying information therein. This manifest is preferably in a computer readable medium. The driver usually verifies the totes and signs that he or she has received them. The driver then organizes the totes for delivery (Step P24). More preferably, the totes and the delivery vehicles include tags and/or tag readers in communication with the computer system to allow tracking of prescription orders through this phase of the distribution process.

Upon delivery of the tote to the healthcare facility, a healthcare worker usually inspects the prescription orders and related manifest to determine if these materials are in order (Step P25). If so, the healthcare worker signs that he or she has received them, and then transfers the individual prescription orders to a holding area for distribution to individual patients within the healthcare facility (Step P26).

If not, the healthcare worker has a number of options including preparing an exceptions list (step P27), notifying the remote pharmacy of the discrepancy (step P28), and/or determining the criticality of the discrepancy (step P29). If the discrepancy is critical, the pharmacy can refill the missing or erroneous prescription order (step P8). If the discrepancy is not critical, steps P30 through P36 or the like can be taken.

B. Filling at Remote Filling Facility

If in Step P20, the pharmacy worker determines that the prescription order should be filled at an off site remote filling facility, the prescription order is transmitted to an off-site facility, usually electronically as shown in FIG. 2. In such case, the remote filling facility will attach a new tag to the prescription order, and if equipped with one, may code the tag's read-writable memory 52 (FIG. 1) with appropriate drug identifying and other information about the prescription order.

At the remote filing facility, the prescription order is filled in compliance with traditional filling practices, procedures and regulations, including conducting an initial review, checking insurance, labeling, data entry, filling, and verification (Step P21). The filled prescription order is then combined with other filled prescription orders to be delivered to the pharmacy and transported essentially in bulk to the pharmacy as shown in FIG. 2. Alternatively, the filled prescription orders may be delivered directly to the healthcare provider's facility (step P11) preferably though a delivery system substantially similar to those previously described in steps P23-P36.

Upon arrival at the pharmacy or healthcare provider's facility, the bulk shipment of filled prescription orders are preferably positioned in bulk within an interrogation zone of the computer system (Step 22), which simultaneously reads the tag 16 on each prescription order in the bulk shipment as shown in FIG. 3, and updates the computer system's records with this information, including any new information added by the remote filling facility to the tag's memory 52 (FIG. 1).

2. Pharmacy Tracking Zones

In practice and referring specifically to FIG. 5, it is more efficient to perform the various steps noted above at spaced apart locations, or zones, throughout the pharmacy. For example, prescription order intake (Step P1 of FIG. 6) and initial review (Step P3 of FIG. 6) can be performed at location 21 (FIG. 5). Label printing and data entry (Step P8 of FIG. 5) could be accomplished at location 27 (FIG. 5). Prescription orders waiting from some form of call back either from the customer, the insurer, or the health care provider could be placed at location 27 (FIG. 5). Orders waiting to be filled could be placed at location 28 (FIG. 4), orders waiting pharmacist review and approval could be place at location 23 (FIG. 4), and approved filled prescription orders could be stored at location 30 (FIG. 4). Obviously, additional zones (24 & 28) could be added to accommodate a particular pharmacy's practices and procedures.

Preferably each station includes a tag reader 18 in communication with the computer system 20 for automatically detecting the arrival of the tag 16 attached to the prescription order 12 as it enters each location. More preferably, the tag reader 18 detects both the arrival of the tag 16 in that station, and the departure of that tag 16 from that station, with the time interval at that station being determined and recorded therefrom.

Each tag reader 18 is preferably fixed at a particular location so that detecting the presence of a tag near the device also automatically indicates the location of that tag 16 within the pharmacy. The tag readers 18 can be rigidly mounted to a work area or station, or portable (i.e. handheld) devices that are operably connected to the station so that it can indicate a location within the pharmacy of a detected tag. Such portable devices facilitate scanning of prescription orders that are compiled in bulk, such as a container of filled prescriptions arriving from an off-site filing facility (Step P22, FIG. 6). Since each prescription order in the container has a unique tag 16 the tag reader 18 can simultaneously detect and record the location of multiple prescription orders, a pharmacy worker can wave the tag reader 18 over the container to record the location of all prescription orders in the container and obtain information recorded in the read-writable memory of each tag.

Similarly, a healthcare worker at a healthcare facility can use the same or a similar system within the healthcare facility to wave a tag reader over a container to record the location of all prescription orders in the container and obtain information recorded in the read-writable memory of each tag.

3. Storage Bin

Space and efficiency can be optimized by storing filled or prescription orders 12 to be held for bulk distribution to the healthcare facility 17 a common storage bin 30, preferably containing a plurality of individually identified cubbies therein.

4. Portable Prescription Order Distribution Cart and Storage Bin

Figure 6B:
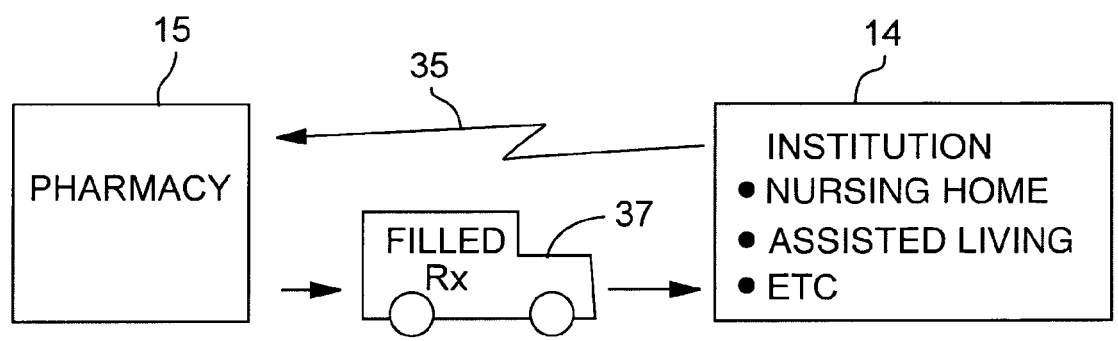
FIG. 6B is a schematic diagram of an exemplar health car provider prescription order filling system showing a possible distribution of a prescription order from the remote pharmacy of FIG. 6A to the health care provider for further distribution to a patient or resident.
Figure 7:
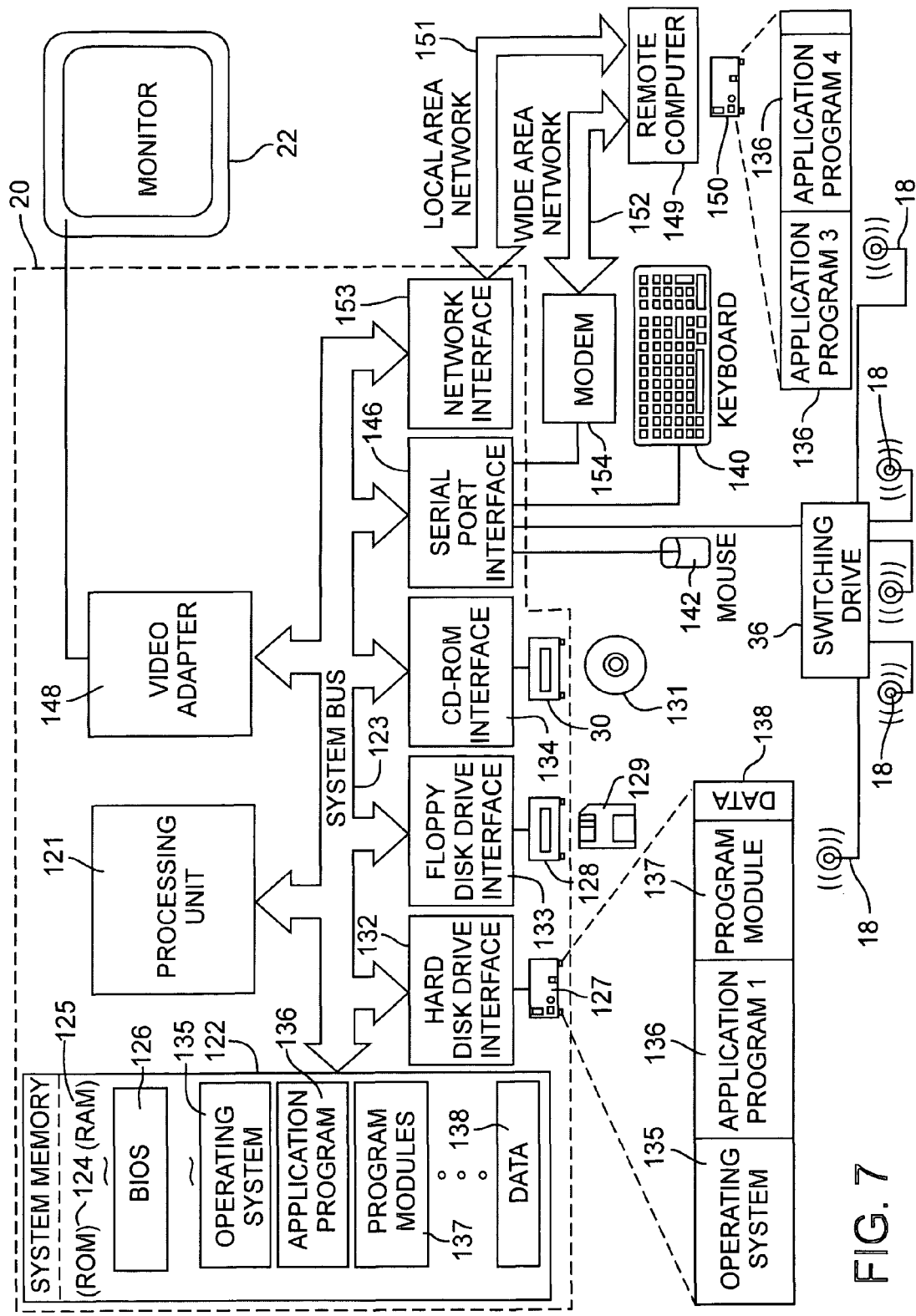
FIG. 7 is a block diagram of an exemplary computer system in accordance with a preferred embodiment of the present invention.

Preferably, and as best shown in FIGS. 6A & 6B, the filled prescription orders for a particular healthcare facility are preferably distributed in bulk to the healthcare facility where they are separated and individually administered to the correct patients. Preferably, the healthcare facility includes tag readers in communication with either their own computer system or the same computer system of the pharmacy to allow the information associated with the tags to be transmitted to the healthcare facility along with the filled prescription orders. Alternatively, if the tags include read-writeable memory, the memory of each tag includes appropriate identifying information to correlate each filled prescription order with a particular patient.

Preferably, the healthcare facility has either a storage bin or a portable storage cart for easy storage, location, and removal of each patient's filled prescription order upon receipt from the remote pharmacy. Both of these storage devices are discussed in greater detail below.

a. Storage Bin

Figure 14:
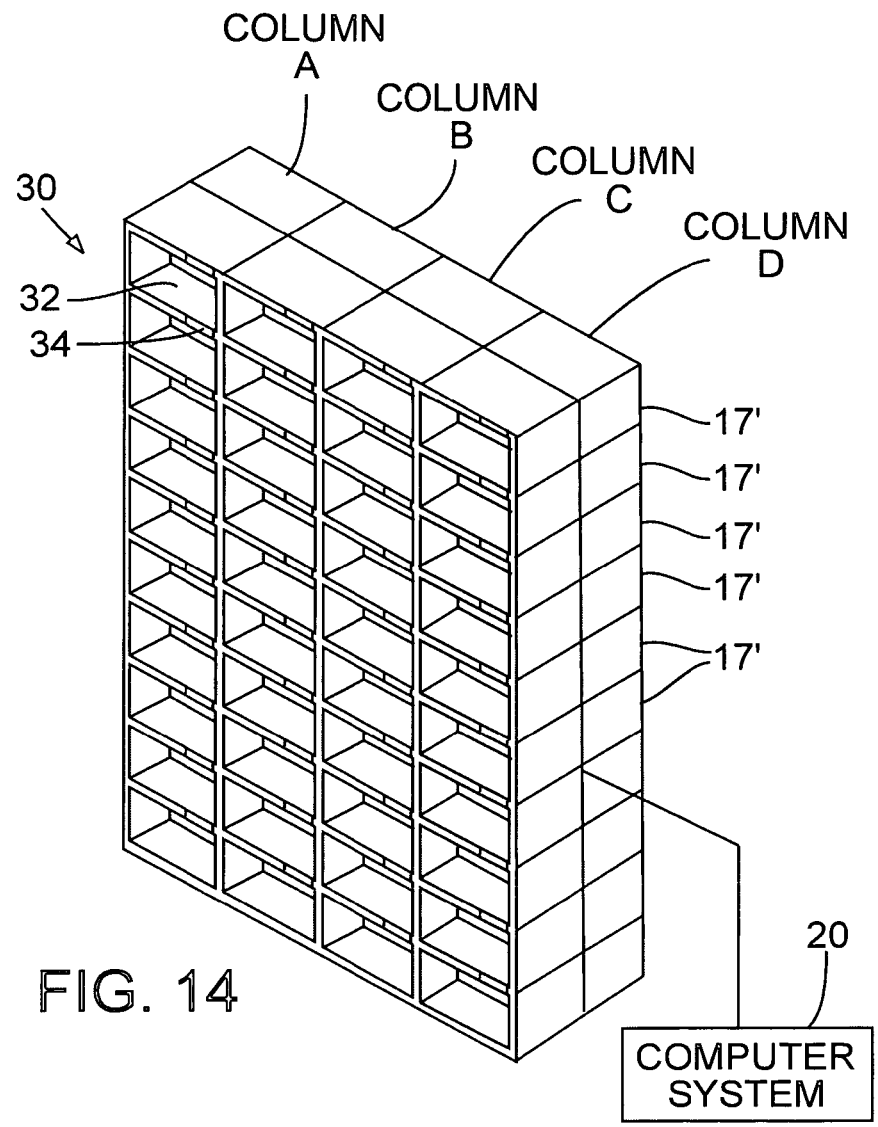
FIG. 14 is a front, isometric view of a storage structure having a plurality of antenna array cards operably secured thereto.

As best shown in FIGS. 14-16, the storage bin 30 preferably includes a plurality of cubbies 32, with each cubby 32 being sized to receive a prescription order 12 and associated filled prescription therein. Each cubby is uniquely identified 34, such as by being individually numbered, and includes a tag reader 18, which is preferably an economical antenna or the like operably secured to a common tag reading device by a switching device 36 (which is also commonly known as a multiplexer) for determining whether a particular tag 16 is received within it. Each tag reader 18 is preferably periodically in communication with the computer system 20.

When a prescription order 12 is filled, the prescription order 12 and filled prescription are simply inserted into an available cubby 32. Accordingly, the tag reader 18 associated with that cubby 32 sends a signal to the computer system 20 denoting the particular location and cubby number where the prescription order 12 and filled prescription are held. When a customer arrives to pick-up his or her filled prescription or when a healthcare provider worker seeks to distribute a particular filled prescription order to a patient, the worker enters the customer's identifying information into the computer system 20, and the particular bin number of the cubby containing the prescription order 12 and filled prescription or the current location in the filling process is displayed. The worker then locates and removes the filled prescription from the identified cubby and presents it to the customer or administers it to a patient as needed.

Alternatively, and/or in addition to determining the cubby number in which the customer's filled prescription order is located, the computer system can activate one or more transducers 17 positioned near the filled prescription order or on the tag 16 secured to the prescription order to alert the worker of its location.

The removal of the prescription order 12 from that particular cubby 32 is detected by the tag reader 18 and reported to the computer system 20. The tag 16 can remain affixed to the prescription order 12, thereby allowing it to be easily located in the future. Alternatively, the tag 16 may be removed from the prescription order and reused with a new incoming prescription order.

b. Portable Prescription Order Distribution Cart

Figure 20:
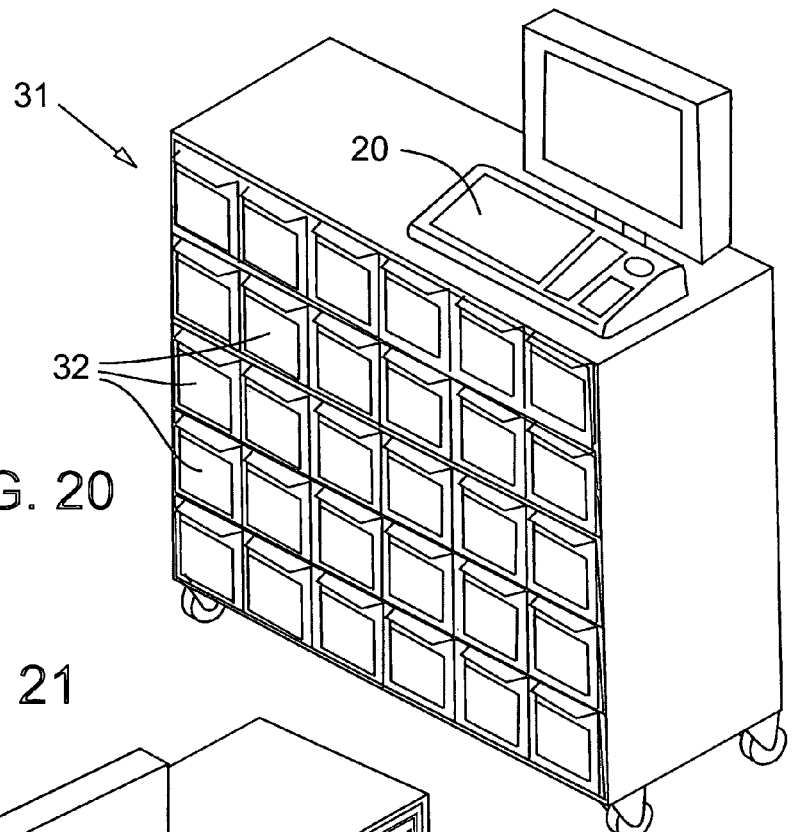
FIG. 20 is a front, isometric view of a portable prescription order distribution cart in accordance with an embodiment of the present invention.
Figure 21:
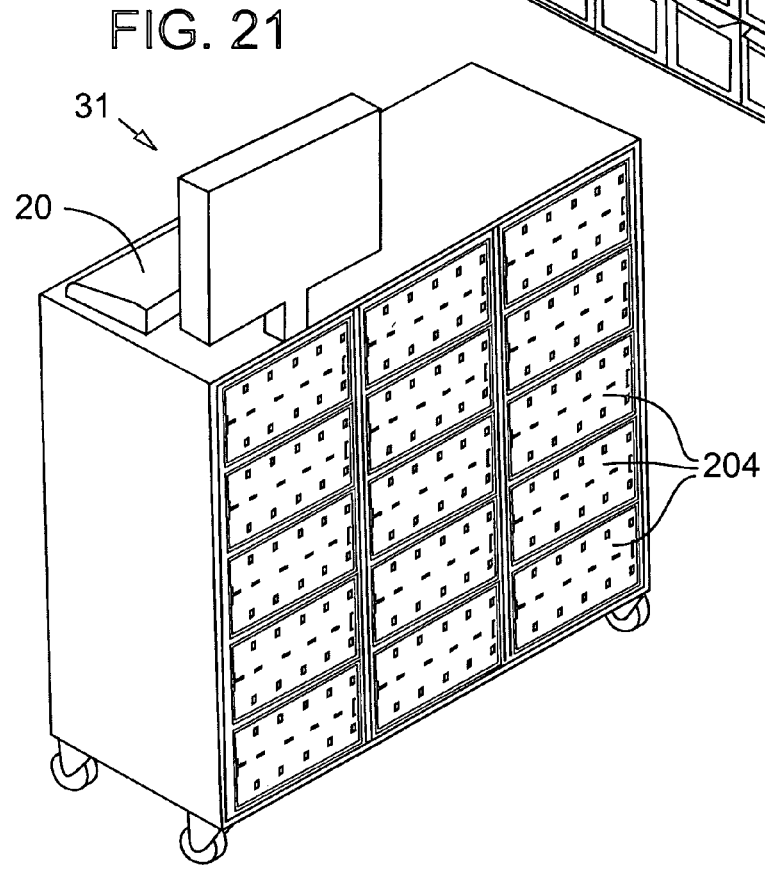
FIG. 21 is a rear, isometric view of the portable prescription order distribution cart in accordance with an embodiment of the present invention.

As best shown in FIGS. 20 & 21, the storage area 30 having a plurality of bins 32 therein can also be made portable, such as by placing it on wheels or casters, thereby defining a portable prescription order distribution cart 31 that may be wheeled room-to-room throughout a healthcare facility 300 to allow easy access to and distribution of filled prescription orders.

Preferably, the portable prescription order distribution cart includes a source of power, such as a battery or the like, an input device such as a mouse and/or keyboard, and a portable tag reader 18 and monitor in communication with the computer system. Accordingly, the cart serves as a stand-alone structure for allowing a worker to easily locate a particular patient's filled prescription orders within a particular bin and administer the filled prescription to the correct patient.

c. Storage Bin Locking Structure

Figure 24:
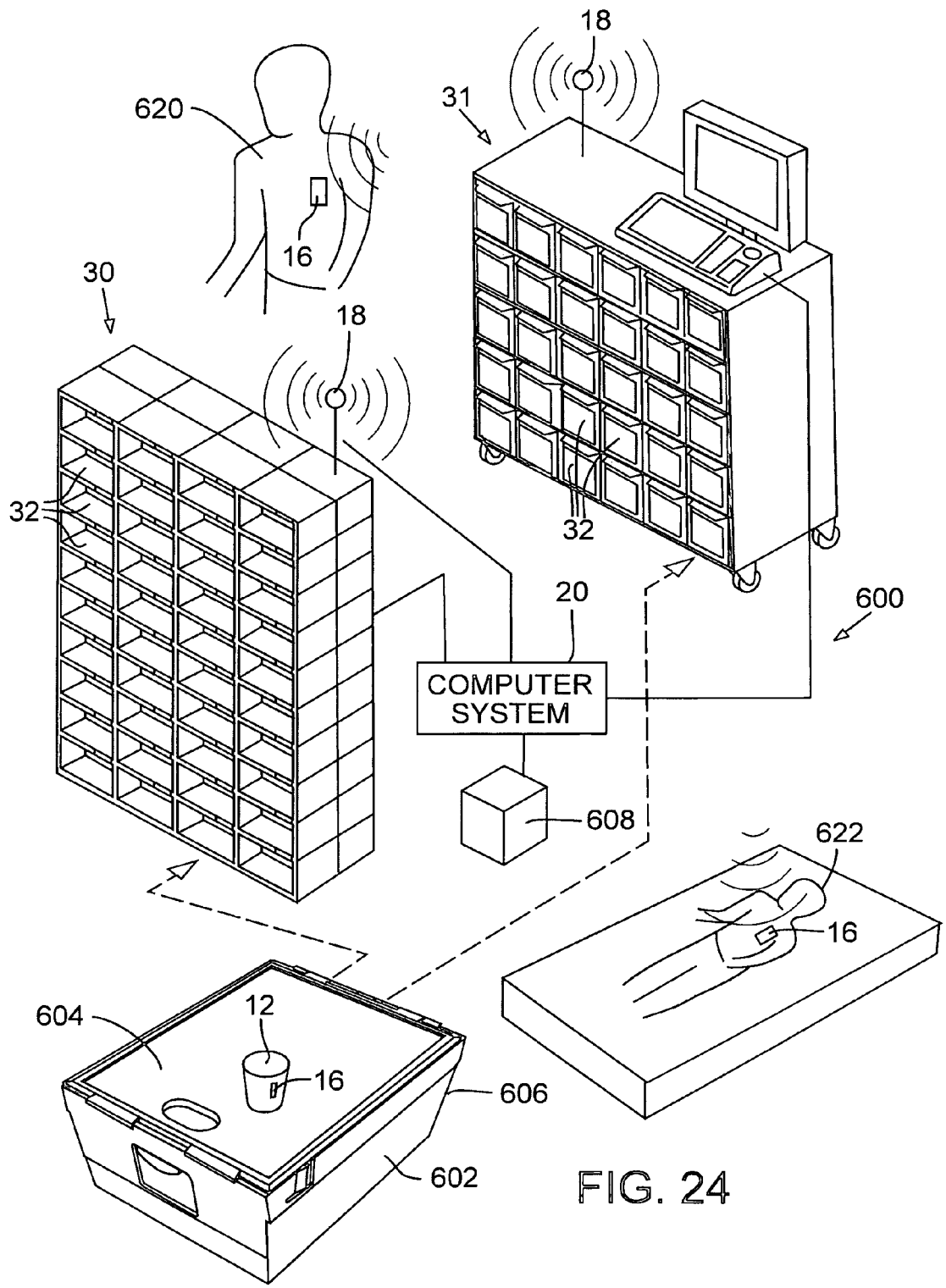
FIG. 24 is an exemplar prescription order storage cabinet locking system in accordance with an embodiment of the present invention.

As shown schematically in FIG. 24, each bin, either in the storage structure 30 or the cart 31 preferably includes a locking structure 600 in communication with the computer system 20 to limit access to filled prescription orders 16 placed therein. For example, a locking tray 602 can operably receive a container 604 having the filled prescription 12 thereon. The tray 602 is sized to secure the container 604 therein and to be slidably received within a bin 32. One or more hooks 606 preferably extend from the tray. The hooks 606 operably engage an electric lock 608 received within or near the bin 32 thereby locking the tray 602 within the bin 32. Accordingly, with the tray 602 locked to the lock 608 within the bin 32 and the container 604 secured within the tray 602, the container 604 cannot be removed from the bin 32.

The electric lock 608 is in communication with the computer system 20 that controls the lock 608 so as to only unlock the tray 602 from the lock 608 when predetermined criteria are met. For example, a worker 620 can wear an identification tag 16 that is detected by a tag reader 18 placed near the bin 32 in which the worker 620 seeks to unlock. The computer system 20 first verifies that the worker 620 is authorized to have access to the items the locked bin, and opens the lock 608 only if the detected worker 620 is authorized. This locking system allows commonly prescribed medications, which are often referred to in the industry as "top 100" medications, to be securely stored within a healthcare facility, but also remain easily accessible to authorized workers, particularly during times when the pharmacy serving the healthcare facility is closed.

In addition, the computer system 20 can release the lock 608 containing the filled prescription only if the patient 622 associated with the prescription order 12 is detected by a tag reader 18 positioned near the locked bin 32 containing the prescription order 12 therein. A tag worn 16 by the patient 622 or some other biometric identification system can be used by the computer system 20 to validate the patient's identity.

C. Proper Distribution Verification

Figure 22:
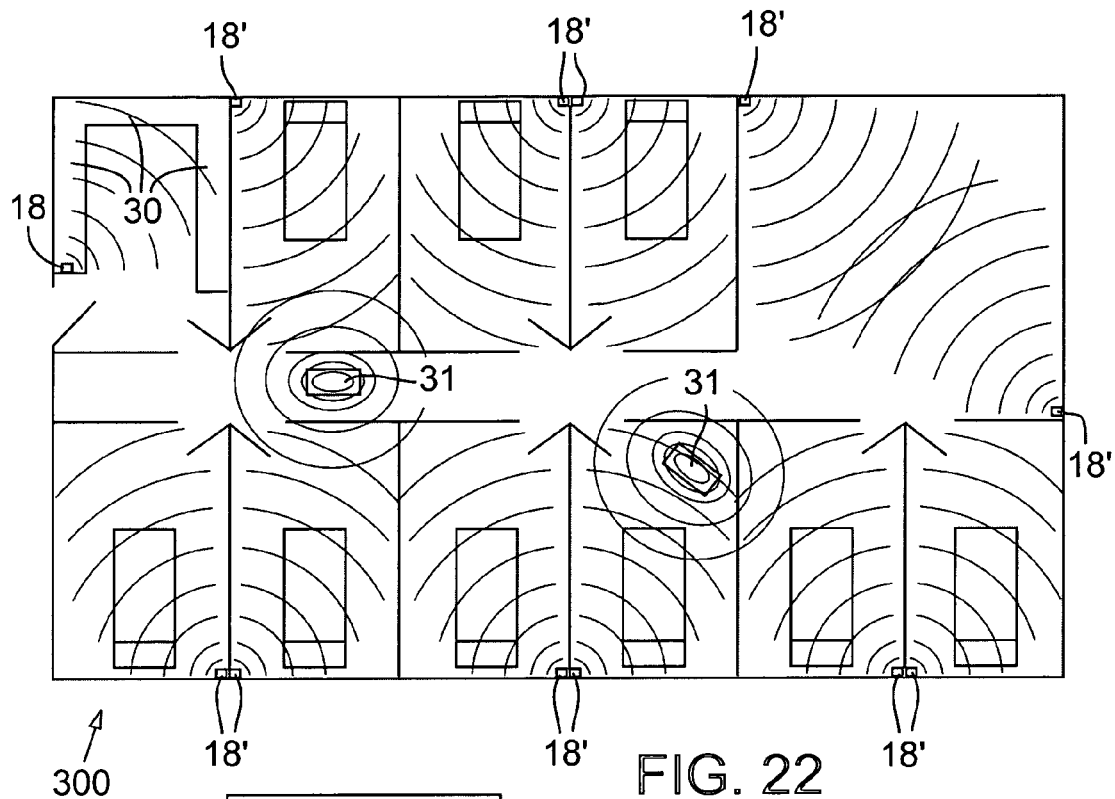
FIG. 22 is a schematic view of a health care provider prescription order tracking system in accordance with an embodiment of the present invention.
Figure 23:
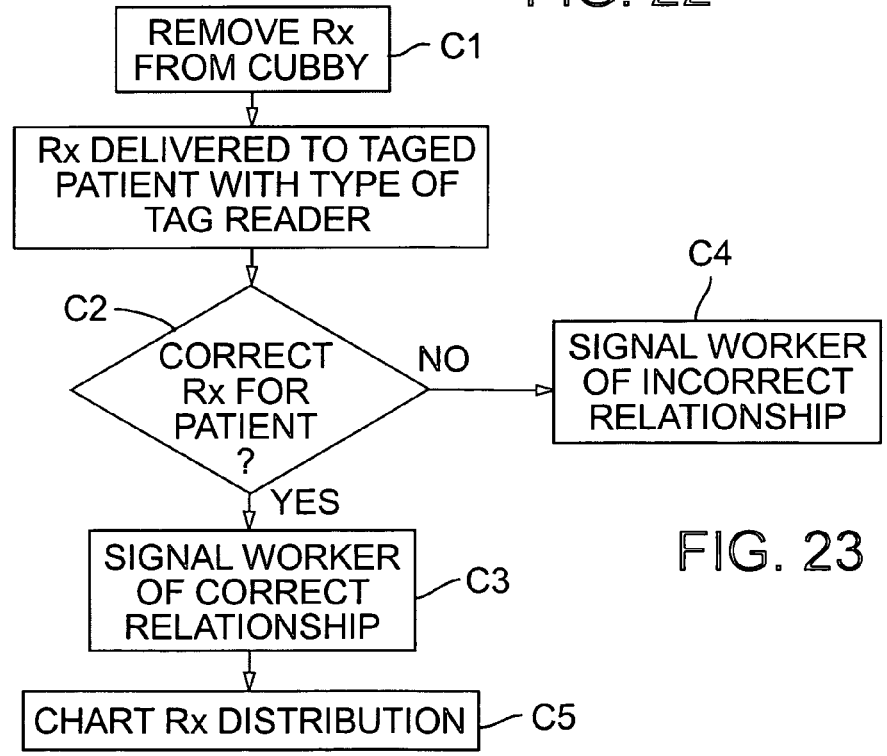
FIG. 23 is an exemplar flow chart of a possible verification system process that automatically verifies that a particular patient within a healthcare facility has been given the correct prescription order for that patient.

Preferably, unique tags are operably secured to the healthcare workers and the patients within a healthcare facility, and these tags are detected by the tag readers positioned on or near the portable cart or within each patient's room as shown in FIG. 22. Accordingly, the information collected and compiled by the computer system 20 can be used to verify that the correct prescription order of a particular patient has been dispensed to the correct patient. A block diagram of an exemplar process and application performing this function is shown in FIG. 23.

The detailed description which follows is represented largely in terms of processes and symbolic representations of operations by conventional computer components, including a processing unit, memory storage devices for the processing unit, and a display device. These operations include the manipulation of data bits by the processing unit and the maintenance of these bits within data structures resident in one or more of the memory storage devices. Such data structures impose a physical organization upon the collection of data bits stored within memory and represent specific electrical or magnetic elements. These symbolic representations are the means used by those skilled in the art of computer programming and the construction of computing devices to most effectively convey teachings and discoveries to others skilled in the art.

For purposes of this discussion, a process is generally a sequence of steps executed by a computing device leading to a desired result. These steps generally require physical manipulations of physical quantities. Usually, although not necessarily, these quantities take the form of electrical, magnetic, or optical signals capable of being stored, transferred, combined, compared, or otherwise manipulated. It is conventional for those skilled in the art to refer to these signals as bits, values, elements, symbols, characters, terms, numbers, records, files or the like. It should be kept in mind however, that these and similar terms should be associated with appropriate physical quantities for computing device operations, and that these terms are merely conventional labels applied to physical quantities that exist within and during operation of the computing device.

It should also be understood that manipulations within the computing device are often referred to in terms such as adding, comparing, moving, etc. which are often associated with manual operations performed by a human operator. The operations described herein are machine operations performed in conjunction with a human operator or user that interacts with a control device. The machines used for performing the operation of the preferred embodiment of the present invention, as will be understood, include a control device and other suitable input devices.

In general, in step C1, within range of a tag reader, a healthcare worker removes a prescription order from a cubby within the portable cart. The computer system detects the removal of the prescription order from the cubby and determines the patient associated with the removed prescription order. The prescription order containing a tag is delivered to a patient within range of a tag reader. In step C2, the computer system detects the tag associated with the patient and the tag associated with the prescription order and determines the identified patient is the correct patient to receive the identified prescription order. If so, transducers, such as lights or sounds, on the portable cart can operate to signal the correct relationship between the prescription order and patient (Step C3). If not, the transducers can operate, usually much more significantly, to indicate an error has been made (Step C4).

If desired, the computer system can also automatically track the time interval between the present prescription order delivery and any prior delivery of the same prescribed medication and compare this time with a predetermined time limit to alert the worker and/or patient that the medication is being administered too soon or too late. Similarly, the computer system can track all medications dispensed to a particular patient and alert a worker and/or the patient if any counter-indicated prescription order combinations have been prescribed to a particular patient.

Also, the computer system can record, or chart, the administration of the prescription order to a patient, thereby saving the healthcare worker time and avoiding the need for the pharmacy worker to manually prepare such reports or charts (Step C5).

Alternatively, the computer system can first detect the presence of a patient 622 within range of the tag reader 18 installed on the cart 31. It then consults an internal database to determine the bin in which that identified patient's prescription order is located, and it can activate one or more transducers positioned on or near that bin to alert the worker of the location of the identified patient's filled prescription order. In cases where locking structures 600 are installed on the bins 32, the computer system 20 can automatically unlock only the bin associated with the identified patient's prescription order, thereby further preventing inadvertent distribution of an improper prescription order by the worker 620.

D. Computer System

Those skilled in the art will appreciate that an exemplary embodiment of the present invention relies on and incorporates several common features of modern personal computers. The general use, operation, and construction of a computer system is known and has been disclosed in numerous patients such as U.S. Pat. No. 5,818,447 to Wolf et al. and U.S. Pat. No. 5,752,025 to Shakib et al.

Referring to FIG. 6, the following discussion is intended to provide a brief, general description of a suitable computing environment in which the invention may be implemented. Although not required, the invention will be described in the general context of computer-executable instructions, such as program modules, being executed by a personal computer. Generally, program modules include routines, programs, objects, components, data structures, etc. that perform particular tasks or implement particular abstract data types. Moreover, those skilled in the art will appreciate that the invention may be practiced with other computer system configurations, including hand-held devices, multiprocessor systems, microprocessor-based or programmable consumer electronics, network PCs, minicomputers, mainframe computers, and the like. The invention may also be practiced in distributed computing environments where tasks are performed by remote processing devices that are linked through a communications network. In a distributed computing environment, program modules may be located in both local and remote memory storage devices.

With reference to FIG. 6, an exemplary system for implementing the invention includes a general purpose computing system in the form of a conventional personal computer 20, including a processing unit 121, a system memory 122, and a system bus 123 that couples various system components including the system memory to the processing unit 121. The system bus 123 may be any of several types of bus structures including a memory bus or memory controller, a peripheral bus, and a local bus using any of a variety of bus architectures. The system memory includes read only memory (ROM) 124 and random access memory (RAM) 125. A basic input/output system 126 (BIOS), containing the basic routines that help to transfer information between elements within the personal computer 20, such as during start-up, is stored in ROM 124. The personal computer 20 further includes a hard disk drive 127 for reading from and writing to a hard disk, not shown, a magnetic disk drive 128 for reading from or writing to a removable magnetic disk 129, and an optical disk drive 130 for reading from or writing to a removable optical disk 131 such as a CD ROM or other optical media. The hard disk drive 127, magnetic disk drive 128, and optical disk drive 130 are connected to the system bus 123 by a hard disk drive interface 132, a magnetic disk drive interface 133, and an optical drive interface 134, respectively. The drives and their associated computer-readable media provide nonvolatile storage of computer readable instructions, data structures, program modules and other data for the personal computer 120. Although the exemplary environment described herein employs a hard disk, a removable magnetic disk 129 and a removable optical disk 131, it should be appreciated by those skilled in the art that other types of computer readable media which can store data that is accessible by a computer, such as magnetic cassettes, flash memory cards, digital video disk, Bernoulli cartridges, random access memories (RAMs), read only memories (ROM), and the like, may also be used in the exemplary operating environment.

A number of program modules may be stored on the hard disk, magnetic disk 129, optical disk 131, ROM 124 or RAM 125, including an operating system 135, one or more application programs 136, other program modules 137, and program data 138. A user may enter commands and information into the personal computer 20 through input devices such as a keyboard 140, pointing device 142, and tag readers 18. Other input devices (not shown) may include a microphone, joystick, game pad, satellite dish, scanner, or the like.

These and other input devices are often connected to the processing unit 121 through serial port interface 146 that is coupled to the system bus, but may be connected by other interfaces, such as a parallel port, game port or a universal serial bus (USB). A display 22 or other type of display device is also connected to the system bus 123 via an interface, such as a video adapter 148. In addition to the monitor, personal computers typically include other peripheral output devices (not shown), such as speakers and printers.

The personal computer 20 may operate in a networked environment using logical connections to one or more remote computers, such as a remote computer 149. The remote computer 149 may be another personal computer, a server, a router, a network PC, a peer device, a personal digital assistant ("PDA"), or other common network node, and typically includes many or all of the elements described above relative to the personal computer 20, although only a memory storage device 150 has been illustrated in FIG. 7. The logical connections depicted in FIG. 7 include a local area network (LAN) 151 and a wide area network (WAN) 152. Such networking environments are commonplace in offices, enterprise-wide computer networks, intranets and the Internet.

When used in a LAN networking environment, the personal computer 20 is connected to the local network 151 through a network interface or adapter 153. When used in a WAN networking environment, the personal computer 20 typically includes a modem 154 or other means for establishing communications over the wide area network 152, such as the Internet. The modem 154, which may be internal or external, is connected to the system bus 123 via the serial port interface 146. In a networked environment, program modules depicted relative to the personal computer 20, or portions thereof, may be stored in the remote memory storage device. It will be appreciated that the network connections shown are exemplary and other means of establishing a communications link between the computers may be used.

Preferably, a plurality of networked personal computers 20 are positioned within the pharmacy, one at the intake area (21, FIG. 5), one at the customer pick-up area (29, FIG. 5), and one at the data entry/label area (27, FIG. 5).

E. Multiplexing Tag Reader Array

Referring to FIGS. 5, 8-17, and 20-22, a plurality of tag readers 18, which are distributed throughout the pharmacy 14, healthcare facility, storage device and/or portable cart, are preferably integrated with a switching device 36 that periodically monitors the status of each tag reader 18 and transmits that information to the personal computer 20.

Figure 8:
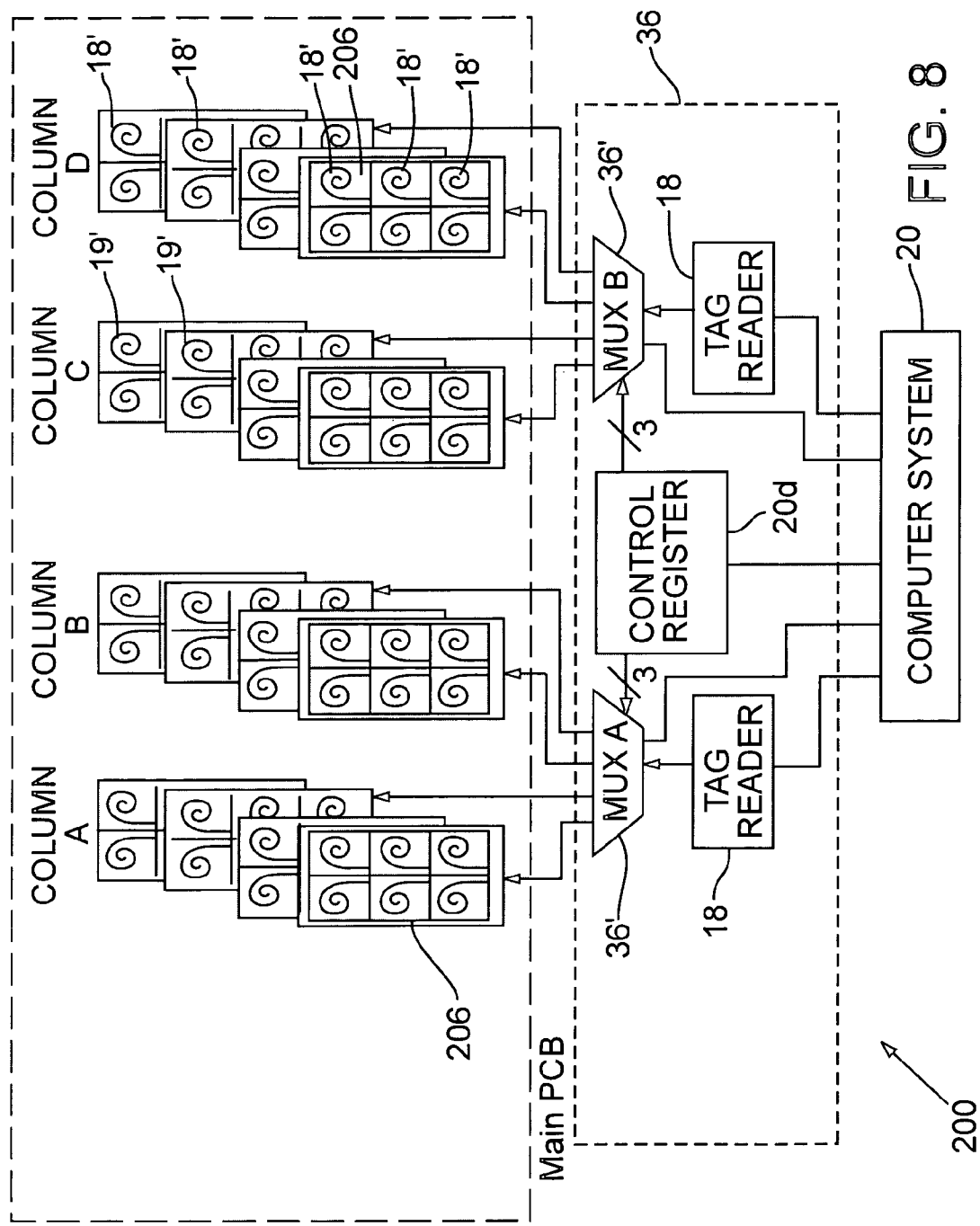
FIG. 8 is an exemplar schematic diagram of a multiplexed tag reader array and related system in accordance with an embodiment of the present invention.
Figure 9:
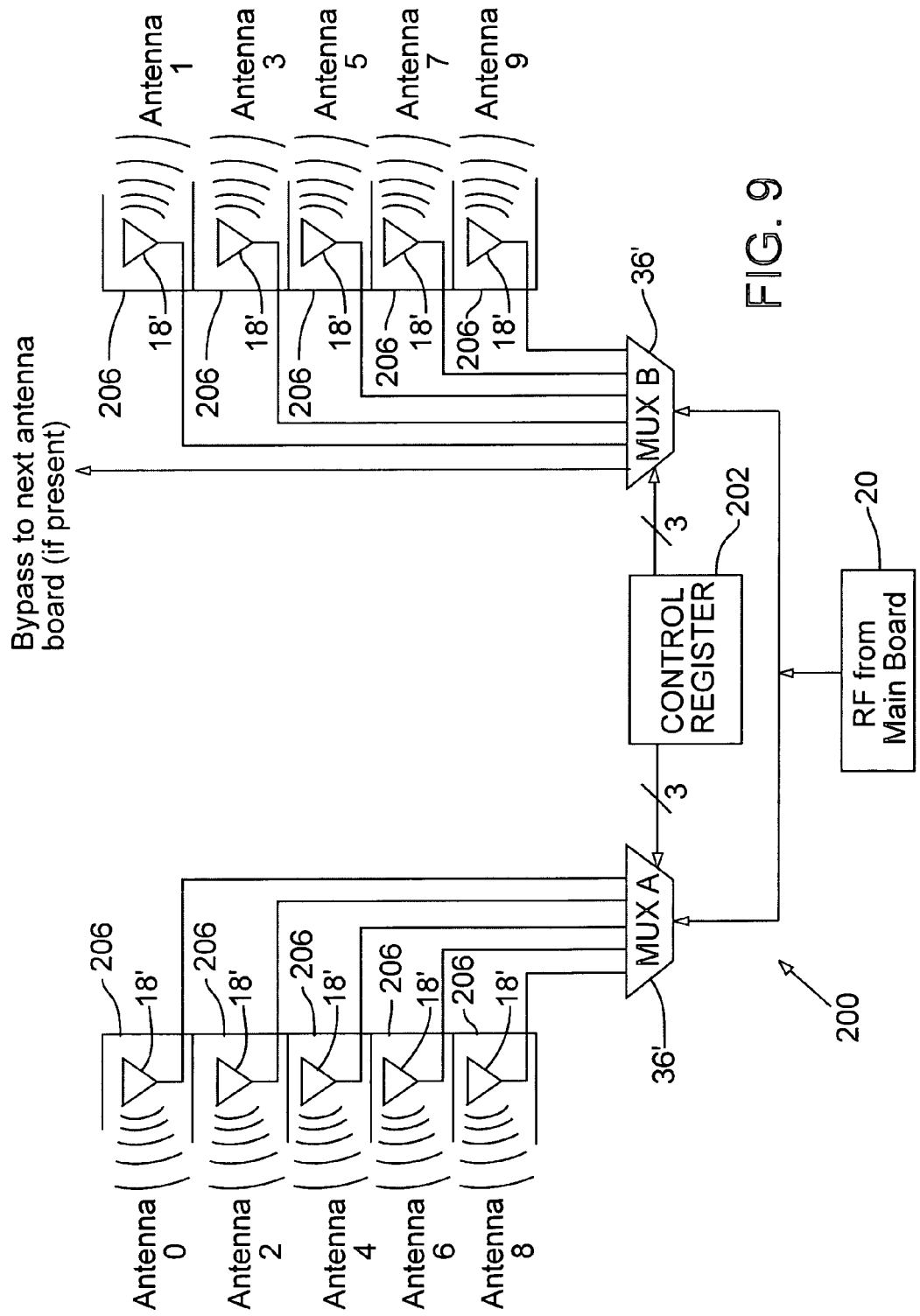
FIG. 9 is an alternative exemplar schematic diagram of a multiplexed tag reader array and related system.
Figure 12:
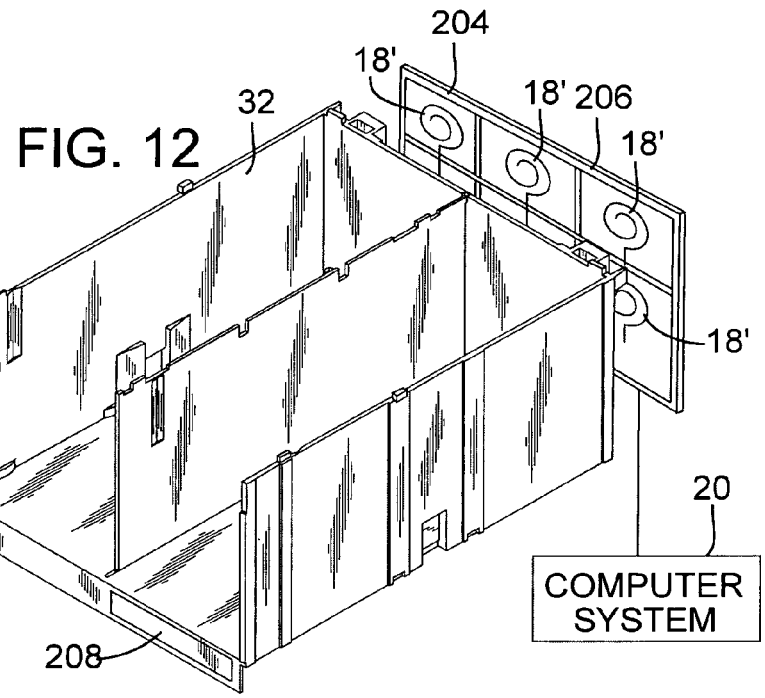
FIG. 12 is a front isometric, exploded view of a storage bin having an antenna array card operably secured thereto.
Figure 13:
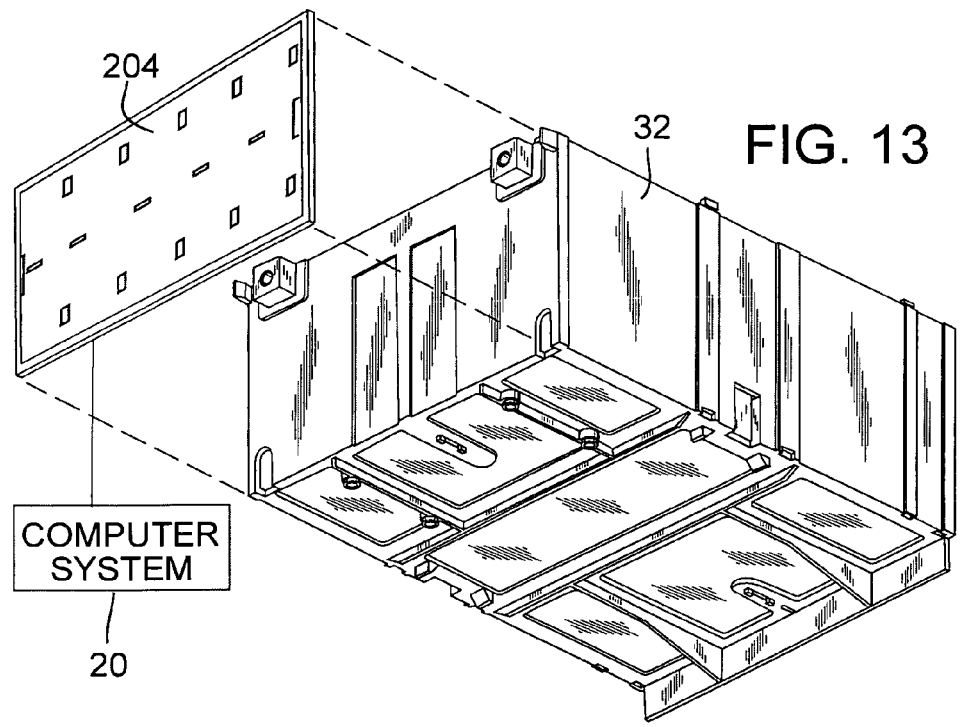
FIG. 13 is a rear, isometric, exploded view of the storage bin and antenna array card of FIG. 12.

An exemplar multiplexing system 200 is disclosed in FIGS. 8 & 9. Preferably, the antenna 18' of each tag reader 18 is operably secured to a multiplexer 36'. Such multiplexers 36' are commonly known to those skilled in the art. A plurality of antenna 18' are operably secured to the multiplexer 36' such that the multiplexer 36' connects each antenna 18' one-by-one to the tag reader 18. Each antenna 18' is positioned at a specific location within the pharmacy 14. For example, one or more antenna 18' can be positioned adjacent to a particular work area 97 upstream of the storage area 30, or can be positioned adjacent to a particular cubby 32 in the storage area 30. A control register 202 monitors which antenna 18' is connected to the tag reader 18 at a given time and provides this information to the computer system 20, which also detects a tracking signal from the tag reader 18 to determine the presence and a tag and thereby determine its location within the pharmacy 14.

Preferably, and as best shown in FIGS. 10-13, a plurality of antenna 18' are formed onto a substantially planar frame 204 with a signal shielding structure 206 encircling one or more antennas 18'. For example, the antenna 18' can be a coil aligned on the planar frame 204 and the signal-shielding structure 206 can be a short circuit encircling the coil on the planar frame 204. Accordingly, the interrogation field of the antenna 18' is directed substantially perpendicular to the planar frame 204. Accordingly, a large number of antenna 18' can be concentrated within a small area, say for example, in a will-call storage device, with each antenna detecting the presence of a tag only if placed within a cubby immediately adjacent to the antenna 18'. Alternatively, the shielding structure can be an electrically grounded frame that surrounds an area in which an interrogation field of a tag reader is directed.

Preferably, the tags operate at a relatively low frequency band of around 13.56 megahertz (MHz). This frequency has been found to allow a plurality of tags within a small area to each be detected by a common tag reader. Moreover, tags operating at about this frequency are able to penetrate through liquids and other materials commonly found in a pharmacy without adversely affecting the tracking performance of the tag.

Although less desirable, the tags operating at an ultra-low frequency such as in the range of about 125 kilohertz (kHz) to about 134.2 kilohertz (kHz) or in the ultra-high frequency band of between about 860 megahertz (MHz) to 960 megahertz (MHz) can also be used.

Figure 17A:
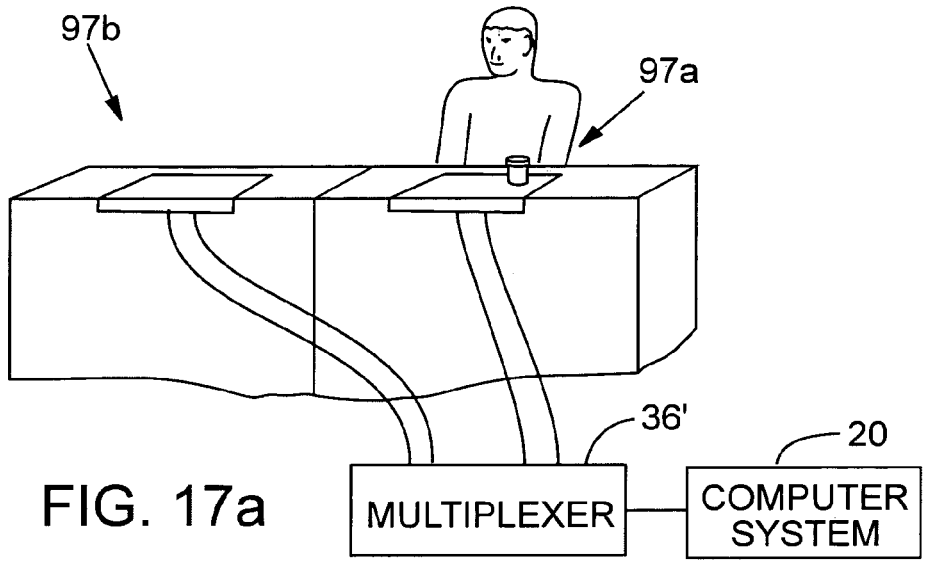
FIG. 17a is an exemplar, isometric view of a possible workstation having a substantially horizontally mounted planar frame containing at least one tag reader antenna therein.
Figure 18:
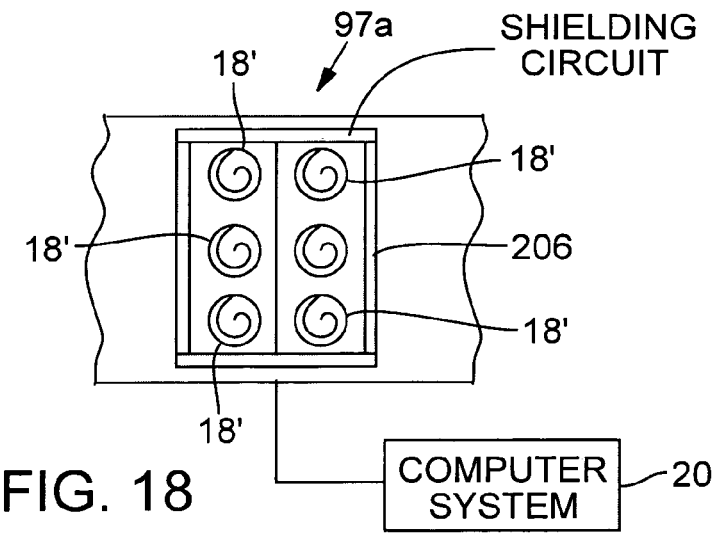

Alternatively, the planar frame 204 containing one or more antenna 18' may be positioned substantially horizontally on a work area 97a, 97b as shown in FIGS. 17a, 17b & 18 with the fields of the antenna directed substantially upward (FIG. 17a) or downward (FIG. 17b). In such case, the signal shielding structure 206 need not necessarily encircle each individual antenna 18' on the frame 204 as shown in FIG. 10. Rather, if needed the shielding structure 206 can encircle the entire frame 204 as best shown in FIG. 18 thereby defining a particular work area 97a and preventing the antenna 18' from inadvertently detecting the presence of a tag in an adjacent work area 97b.

Moreover, and referring to FIGS. 19a & 19b, a plurality of antenna can be positioned around a scanning area and all directed within that area to form a defined space or tunnel 600 in which tags placed therein are scanned by signals generated from a plurality of antenna. Such a scanning tunnel allows for more accurate detection of all tags, particularly when a plurality of tags are grouped together, such as in a bulk shipment received from a remote pharmacy or other off site location.

If desired, the exterior of the storage area can include transducers 17' thereon, such as lights, speakers, or the like that are in communication with the computer system to alert a worker of the location of a particular prescription order. Similarly, each cubby of the storage device can also include transducers 17' thereon to perform a similar function.

In view of the wide variety of embodiments to which the principles of the invention can be applied, it should be apparent that the detailed embodiments are illustrative only and should not be taken as limiting the scope of the invention. For example, although the preferred tags have a read-write feature, a less complex "read-only" tag may also be used in some situations. For example, the computer system can correlate a particular "read only" code on a tag with one or more aspects of the prescription order and/or person to which it is associated with, and use this correlation throughout the tracking system. Rather, the claimed invention includes all such modifications as may come within the scope of the following claims and equivalents thereto.

What is claimed is:

1. A prescription order tracking system for tracking a prescription order through distribution, said prescription order tracking system including:
    a computer readable and wireless first tag operably secured to the prescription order;
    a tag reader in communication with a computer system, said tag reader having a defined area near said tag reader wherein said computer system detects the presence of said first tag within said defined area;
    a storage area having a plurality of spaced apart cubbies therein, each said cubby of said plurality of spaced apart cubbies having a unique visual identifier; and,
    said tag reader positioned adjacent to one cubby of said plurality of spaced apart cubbies such that said defined area is within said one cubby;
    wherein said computer system determines the location of said prescription order by automatically detecting the presence of said first tag within said one cubby and correlating said visual identifier with said prescription order, said automatically detecting the presence of said first tag performed by or under control of the computer system.

2. The prescription order tracking system of claim 1, further including a plurality of tag readers in communication with the computer system, each tag reader of said plurality of tag readers having a unique defined area positioned so as to be substantially limited to an area within a unique cubby of the plurality of cubbies; and,
    wherein said computer system determines which unique cubby of the plurality of cubbies in which a prescription order is placed by automatically detecting the presence of said first tag within one of said plurality of cubbies and correlating the visual identifier associated with said unique cubby in which said first tag is placed.

3. The prescription order tracking system of claim 1, wherein:
    said computer system includes a database identifying a patient associated with the prescription order; and,
    said computer system detects the removal of said prescription order from said one cubby, correlates the identity of the patient with the prescription order, and verifies that the prescription order has been distributed to the patient thereby defining a distribution event.

4. The prescription order tracking system of claim 1, wherein said system is used in a health care facility having a patient therein, said prescription order is for said patient, and said computer system correlates the prescription order with the identity of the patient; wherein said storage area is a movable cart, and said system further includes:
    a second tag reader operably secured to said portable cart defining a scanning area around the cart; and,
    a computer readable and wireless second tag operably secured to said patient within the healthcare facility, said second tag in communication with said computer system and having a unique identifier associated with the identity of the patient;
    such that when the cart is placed near the patient and the prescription order is dispensed from the cart to the patient within said scanning area, the second tag reader detects the first tag operably secured to the prescription order and the second tag secured to the patient and verifies that the identity of the patient associated with the prescription order is the same as the identity of the patient associated with the detected tag.

5. The prescription order tracking system of claim 4, further including a transducer operably secured to the cart and in communication with the computer system for alerting a worker if the identity of the patient associated with the detected second tag is different from the identity of the patient associated with the prescription order.

6. The prescription order tracking system of claim 4, further including a transducer operably secured to the second tag and in communication with the computer system for alerting a worker if the identity of the patient associated with the detected second tag is different from the identity of the patient associated with the prescription order.

7. The prescription order tracking system of claim 4, further including a transducer operably secured to the first tag and in communication with the computer system for alerting a worker if the identity of the patient associated with the detected second tag is different from the identity of the patient associated with the prescription order.

8. The prescription order tracking system of claim 4, further including a computer readable and wireless third tag, said third tag in communication with the computer system and operably secured to the worker dispensing the prescription order from the portable cart and having a unique identifier associated with the identity of the worker; wherein:
   said second tag reader detects the presence of said third tag within the scanning area when said prescription order is dispensed, and records the identity of the worker who dispensed the prescription order to the patient.

9. The prescription order tracking system of claim 1, wherein said system is used in a health care facility having a patient therein, said prescription order is for said patient, and said computer system correlates the prescription order with the identity of the patient; said system further including:
   a second tag reader operably secured within the healthcare facility substantially near the defined area defining a scanning area around the patient;
   said computer system correlating said second tag reader with the identity of the patient;
   such that when the prescription order is dispensed from the cart to the patient, the second tag reader detects the tag operably secured to the prescription order and verifies that the identity of the patient associated with the prescription order is the same as the identity of the patient associated with the second reader.

10. The prescription order of claim 9, further including:
   a computer readable and wireless second tag operably secured to the patient, said second tag in communication with the computer system and associated with the identity of the patient; and,
   the second tag reader detects the first tag secured to the prescription order and the second tag secured to the patent and verifies that the identity of the patient associated with the prescription order is the same as the identity of the patient associated with the detected tag.

11. A method for tracking a prescription order through distribution to a patient within a healthcare facility, said method comprising the steps of:
   tagging the prescription order with a wireless tag readable by a tag reader in communication with a computer system;
   positioning the tag reader within the healthcare facility; said tag reader having a defined area in which the presence of the wireless tag within that region is detectable by the computer system and thereby able to correlate the location of the prescription order within the health care facility;
   moving the prescription order with the wireless tag within the healthcare facility;
   tracking the location of the prescription order within the health care facility by the computer system automatically detecting the tag within the defined area of the tag reader.

12. The method for tracking a prescription order through distribution to a patient within a healthcare facility of claim 11, further comprising the steps of positioning a plurality of tag readers, each spaced apart from the other, throughout the healthcare facility, each tag reader having a unique scanning zone in a separate defined area of the healthcare facility;
   tracking the filled prescription order throughout the healthcare facility by detecting the presence of the tag within one of the separate defined areas of the plurality of tag readers; and,
   the computer system determining the location of the prescription order by correlating the location of the tag reader that detects the presence of the tag with the location of that tag reader.

13. The method for tracking a prescription order through distribution to a patient within a healthcare facility of claim 11, wherein said positioning a tag reader within the healthcare facility step includes operably securing the tag reader to a cart and placing the prescription order within the cart, thereby allowing the tag reader to move with the cart.

14. The method for tracking a prescription order through distribution to a patient within the healthcare facility of claim 11, further including the step of:
   the computer system correlating the prescription order with the identity of the patient associated with the prescription order;
   at the time the prescription order is distributed to the patient, the computer system independently detecting the identity of the patent within the healthcare facility; and,
   the computer system correlating the identity of the patient associated with the prescription order with the detected identity of the patent; and,
   signaling a worker if the detected identity of the patient is different from the identity of the patient associated with the prescription order.

15. The method for tracking a prescription order through distribution to a patient within the healthcare facility of claim 11, wherein the step of the computer system independently detecting the identity of the patent within the healthcare facility includes operably securing a wireless tag to the patient, said wireless tag having a unique identifier associated with the identity of the patient, and readable by the tag reader.

16. The method for tracking a prescription order through distribution to a patient within the healthcare facility of claim 14, further including the step of:
   the computer system automatically recording a distribution event for future retrieval.

17. The portable prescription order tracking system for tracking a prescription order through distribution of claim 1, further including:
   a locking structure for securing said prescription order therein, said locking structure in communication with the computer system;
   said computer system releasing said locking structure in response to predetermined criteria.

18. The prescription order tracking system for tracking a prescription order through distribution of claim 1, wherein said storage area is a moveable cart.

19. The prescription order tracking system for tracking a prescription order through distribution of claim 1, wherein said storage area is operably secured to a frame having at least one wheel for rolling said frame on a floor, thereby making the storage area portable.

20. The prescription order tracking system of claim 1, wherein:
   said computer system includes a memory for storing data related to the prescription order's placement relative to said one cubby, said data selected from the group consisting of the identity of the prescription order, the time the prescription order was placed in said one cubby, the date the prescription order was placed in said one cubby, the time the prescription order was removed from said one cubby, and the date the prescription order was removed from said one cubby.

21. The prescription order tracking system of claim 20, wherein, said computer system includes an interface for detecting the identity of the worker removing the prescription order from said one cubby and said data related to the prescription order's placement relative to the unique cubby includes the identity of the worker removing the prescription order from said one cubby.

22. The prescription order tracking system of claim 21, wherein said interface is a wireless computer readable employee identification tag in communication with the computer system and operably secured to the worker.

23. The prescription order tracking system for tracking a prescription order through distribution of claim 4, wherein the computer system has memory, and data of the distribution event is recorded on said memory, said data of the distribution event is selected from the group consisting of the identity of the worker, the identity of the patient, the prescription order dispensed to said patient, the time the prescription order was dispensed to said patient, the date the prescription order was dispensed to said patient, and the location within the healthcare facility where the prescription order was dispensed.

24. The method for tracking a prescription order through distribution to a patient within the healthcare facility of claim 16, wherein the distribution event includes data selected from the group consisting of the identity of the worker, the identity of the patient, the prescription order dispensed to said patient, the time the prescription order was dispensed to said patient, the date the prescription order was dispensed to said patient, and the location within the healthcare facility where the prescription order was dispensed.

\* \* \* \* \*